US012605091B2

(12) United States Patent
Nabavi et al.

(10) Patent No.: US 12,605,091 B2
(45) Date of Patent: Apr. 21, 2026

(54) SYSTEMS AND METHODS FOR INTRAORAL pH MONITORING

(71) Applicant: Dianyx Innovations, LLC, Westerville, OH (US)

(72) Inventors: Seyedfakhreddin Nabavi, Montreal (CA); Robert Kibler, Columbus, OH (US); John Cogan, Blackrock County (IE); Asim Roy, Dublin, OH (US); Brandon Canfield, Columbus, OH (US); Collin Emerick, Columbus, OH (US)

(73) Assignee: Dianyx Innovations, LLC, Westerville, OH (US)

( * ) Notice: Subject to any disclaimer, the term of this patent is extended or adjusted under 35 U.S.C. 154(b) by 259 days.

(21) Appl. No.: 18/360,506

(22) Filed: Jul. 27, 2023

(65) Prior Publication Data

US 2024/0032824 A1      Feb. 1, 2024

Related U.S. Application Data

(60) Provisional application No. 63/392,548, filed on Jul. 27, 2022.

(51) Int. Cl.
| | |
|---|---|
| *A61B 5/145* | (2006.01) |
| *A61B 5/00* | (2006.01) |
| *A61B 5/263* | (2021.01) |
| *G16H 20/00* | (2018.01) |
| *G16H 50/20* | (2018.01) |

(52) U.S. Cl.
CPC .......... *A61B 5/14507* (2013.01); *A61B 5/263* (2021.01); *A61B 5/682* (2013.01); *A61B 5/742* (2013.01); *G16H 20/00* (2018.01); *G16H*

*50/20* (2018.01); *A61B 2562/063* (2013.01); *A61B 2562/164* (2013.01)

(58) Field of Classification Search
None
See application file for complete search history.

(56) References Cited

U.S. PATENT DOCUMENTS

| | | | | |
|---|---|---|---|---|
| 2023/0190195 A1* | 6/2023 | Kibler | ................ | A61B 5/14552 |
| | | | | 600/301 |
| 2023/0277135 A1* | 9/2023 | Kibler | ................... | G16H 40/63 |
| | | | | 600/301 |

FOREIGN PATENT DOCUMENTS

| | | | | |
|---|---|---|---|---|
| KR | 20080094139 A | * 10/2008 | ........... | G01N 27/302 |

OTHER PUBLICATIONS

Kim KR 20080094139 (Year: 2008).*

* cited by examiner

*Primary Examiner* — Jon Eric C Morales
(74) *Attorney, Agent, or Firm* — Neustel Law Offices

(57)      ABSTRACT

A system and method for monitoring pH of an intraoral device involves receiving the oral pH data from at least one pH sensor embedded within the intraoral device. The oral pH data is then correlated with one or more user related data to classify the oral pH data into one or more pre-defined categories indicative of a health condition. Further, the machine learning module generates feedback and/or recommendations for the user based on the classification of the oral pH data into one or more pre-defined categories. The oral pH data and/or feedback and/or recommendations are then communicated to the user and/or external device.

17 Claims, 16 Drawing Sheets

500

100

Data Management Platform 110

Remote Monitor System 112

Device Management Platform 108

Machine Learning Module 136

Network 114

Intraoral Device 102

Sensors 116

Battery 118

Device Module 120

Docking Station 104

Charging Module 124

Data Module 126

Disinfection Module 128

Power Source 130

Client Device 106

Monitor App 132

Monitor UI 134

200

Minor salivary glands

Parotid salivary glands

Submandibular salivary glands

Sublingual salivary glands

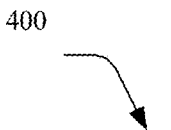
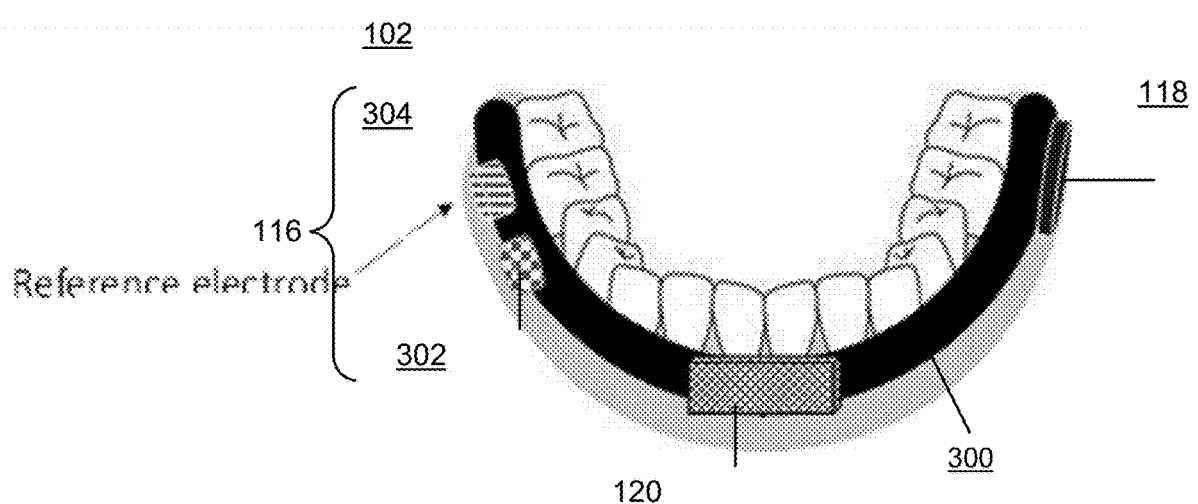
*Fig. 4*

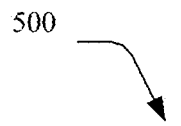
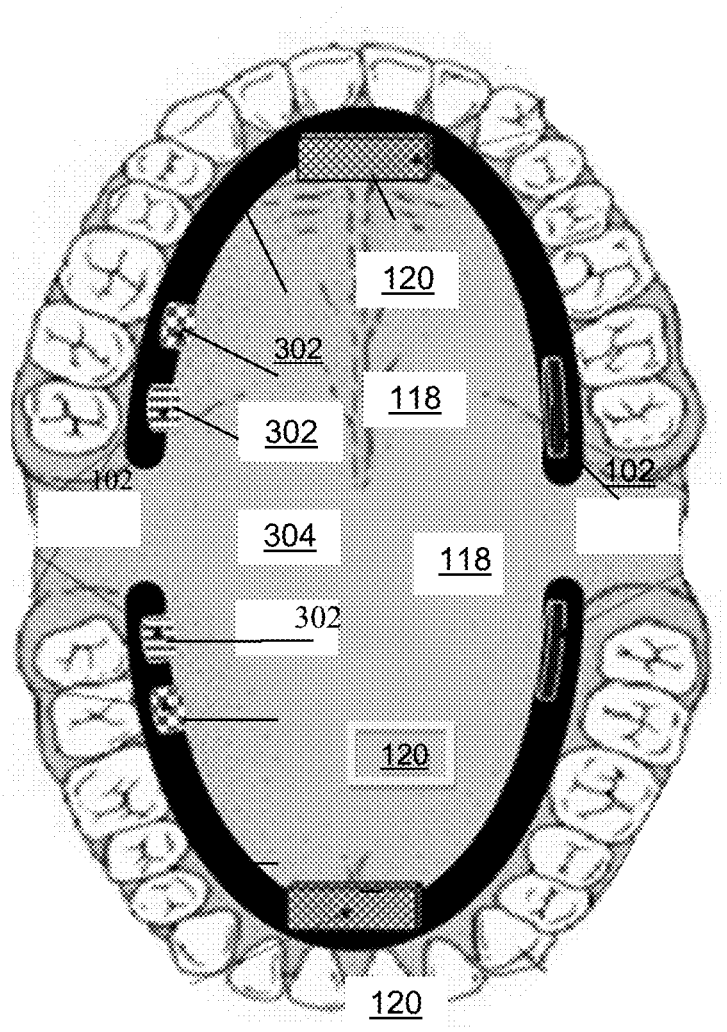
*Fig. 5*

600

600a

600b

600c

600d

Sensing Electrode

Reference Electrode

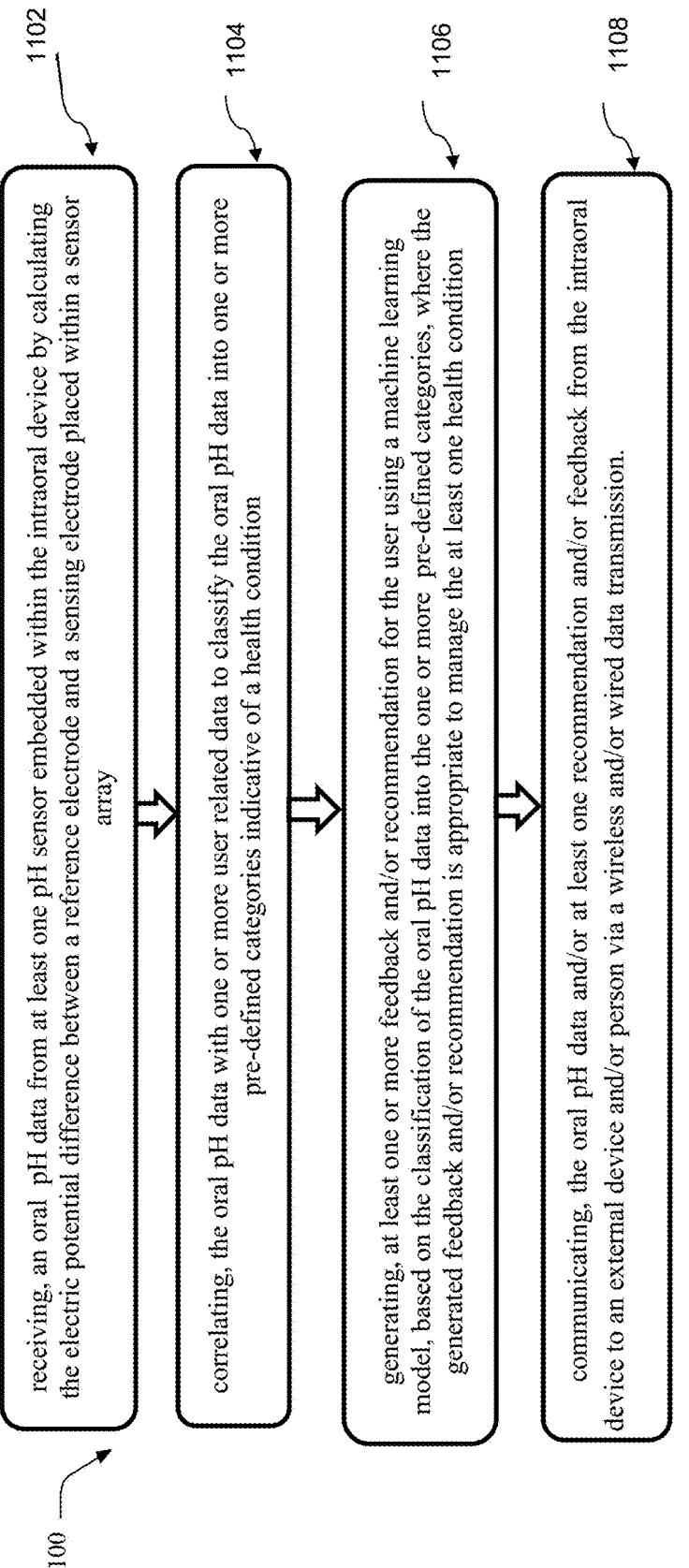

1100

1102 receiving, an oral pH data from at least one pH sensor embedded within the intraoral device by calculating the electric potential difference between a reference electrode and a sensing electrode placed within a sensor array

1104 correlating, the oral pH data with one or more user related data to classify the oral pH data into one or more pre-defined categories indicative of a health condition

1106 generating, at least one or more feedback and/or recommendation for the user using a machine learning model, based on the classification of the oral pH data into the one or more pre-defined categories, where the generated feedback and/or recommendation is appropriate to manage the at least one health condition

1108 communicating, the oral pH data and/or at least one recommendation and/or feedback from the intraoral device to an external device and/or person via a wireless and/or wired data transmission.

*Fig. 11*

1208a
sleep related conditions 1208b
acidic reflux conditions 1208c
non-acidic reflux conditions 1208d
other health condition 1208
Classifying the oral pH data 1206
Correlation and analysis of oral pH data 1204
Receiving oral pH data 1212
recommendations provided back to the user:
" eat less oily food; sleep on your left position "

1210
feedback generated by the device module using machine learning techniques:
"acidic reflux events are monitored due to change in pH values"

1202

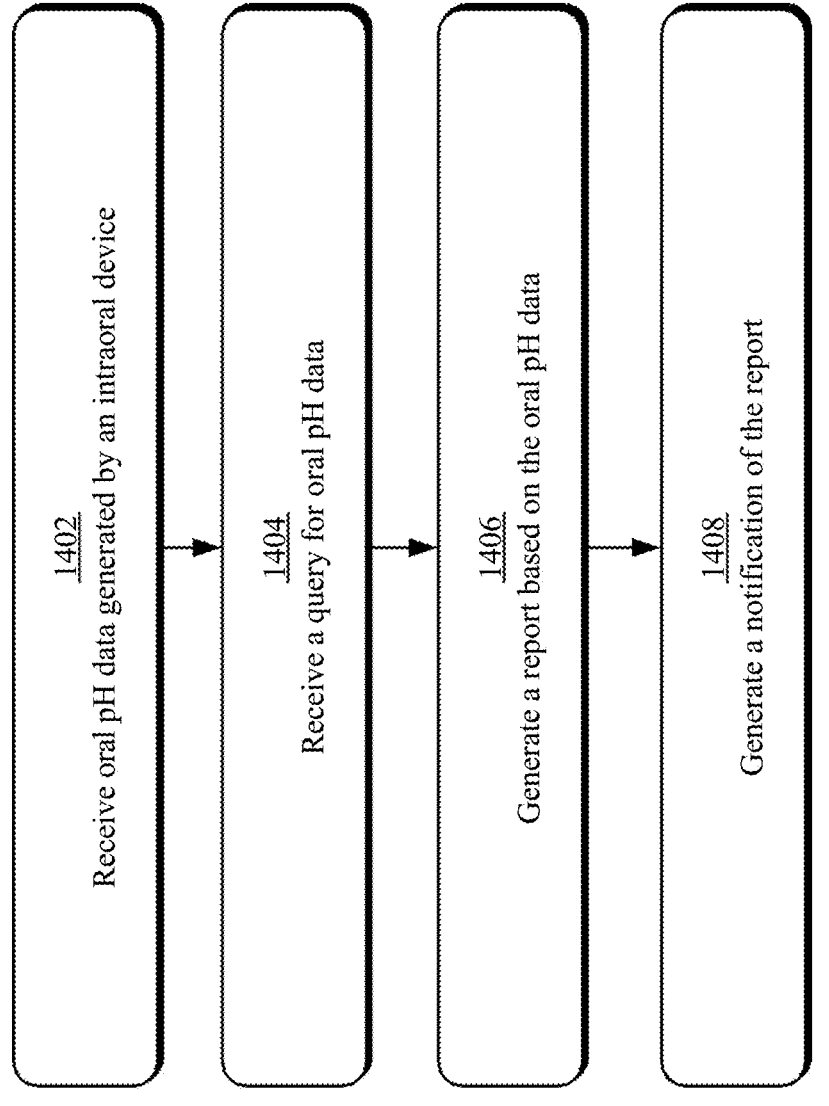
1402
Receive oral pH data generated by an intraoral device
1404
Receive a query for oral pH data
1406
Generate a report based on the oral pH data
1408
Generate a notification of the report
1400
*Fig. 14*

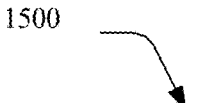
1500
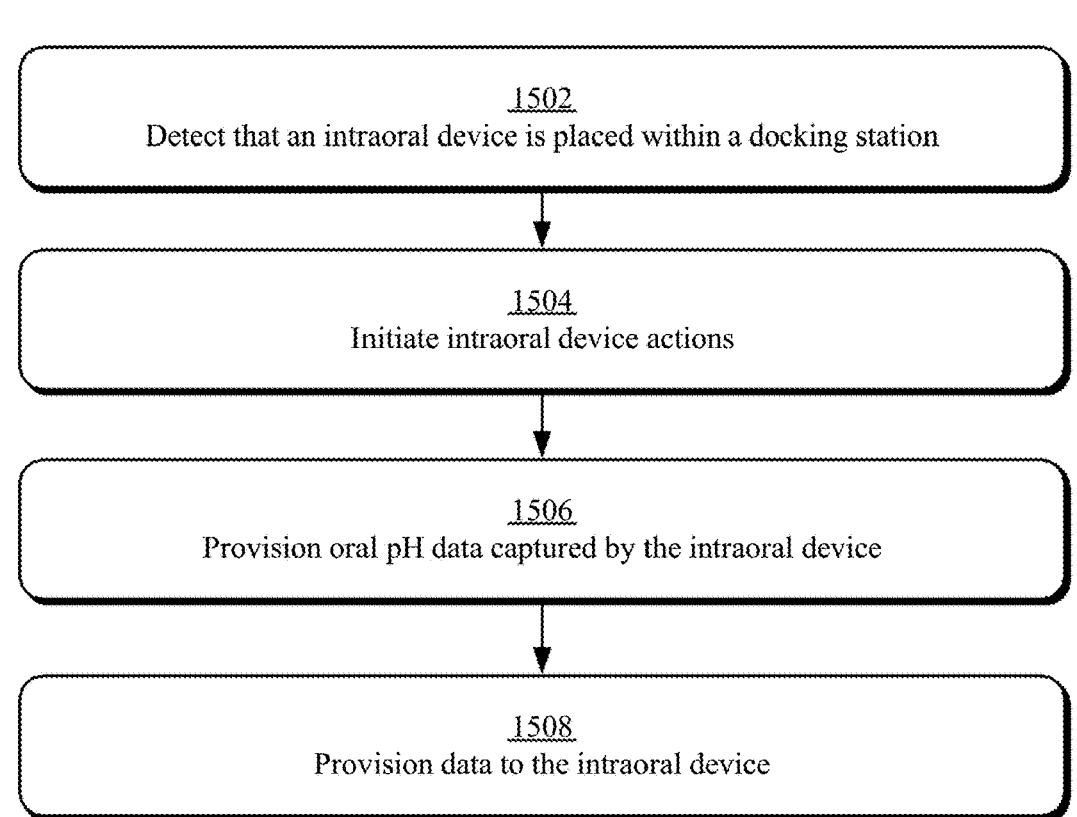
1502
Detect that an intraoral device is placed within a docking station
1504
Initiate intraoral device actions
1506
Provision oral pH data captured by the intraoral device
1508
Provision data to the intraoral device
*Fig. 15*

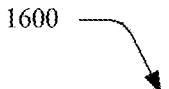

1600

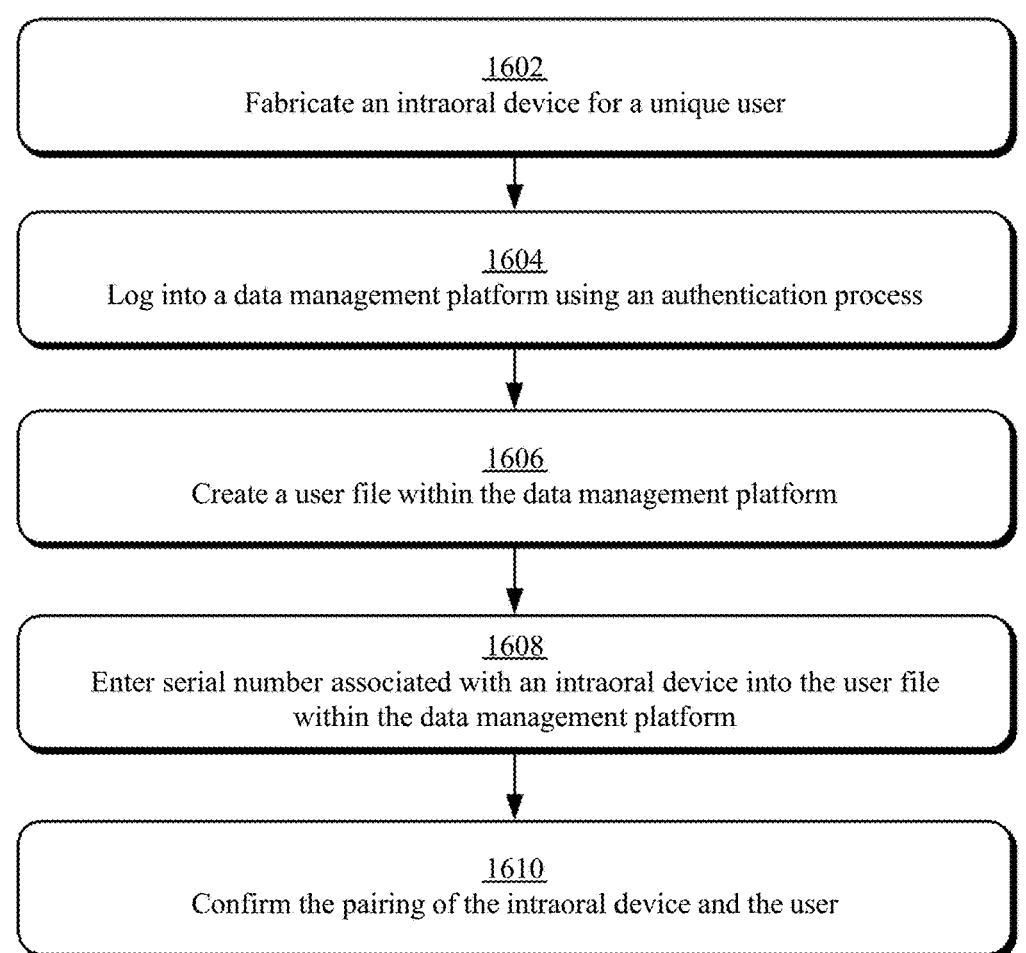

<u>1602</u>
Fabricate an intraoral device for a unique user

↓

<u>1604</u>
Log into a data management platform using an authentication process

↓

<u>1606</u>
Create a user file within the data management platform

↓

<u>1608</u>
Enter serial number associated with an intraoral device into the user file within the data management platform

↓

<u>1610</u>
Confirm the pairing of the intraoral device and the user

*Fig. 16*

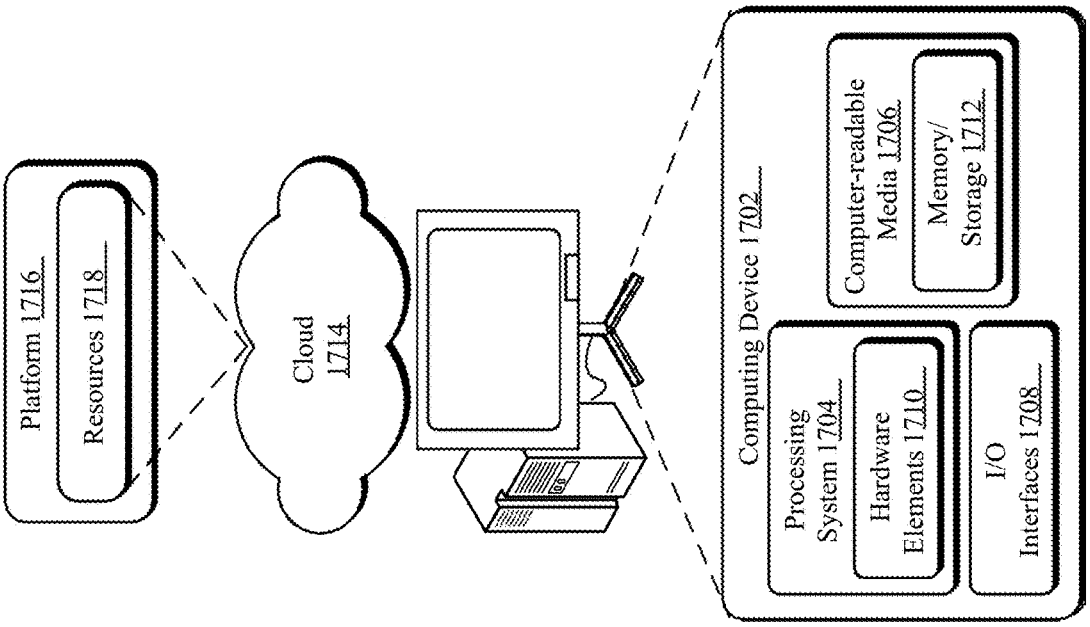
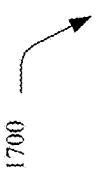
Fig. 17

SYSTEMS AND METHODS FOR INTRAORAL pH MONITORING

TECHNICAL FIELD

The present disclosure relates to systems and methods for intraoral pH monitoring. In particular, the disclosure relates to monitoring the pH of an intraoral cavity or fluids using pH sensor placed within an intraoral device and providing appropriate feedback and/or recommendations to a user that aid in management of the user health condition.

BACKGROUND

The measurement of pH plays a crucial role in clinical practice. pH is the measure of acidity or alkalinity. It can be measured at many different sites in the body and can indicate many different medical conditions. In particular, the pH of saliva measured in the mouth can help to diagnose conditions that are related to breathing and digestion. In another examples, arterial blood pH is measured to determine disease progression in critical illnesses, such as cancer, chronic respiratory diseases and diabetes. In addition, measurement of blood pH is a typical procedure in anesthesia during most surgeries. It has been shown that oral pH is significantly altered in patients suffering from gastroesophageal reflux disease (GERD). Therefore, continuous monitoring of oral pH is a common approach to diagnose GERD. Depending on the breathing routs, i.e., nasal canal or oral cavity, the oral pH can be varied, therefore it can be used for sleep study overnight measurement. Furthermore, salivary pH can be affected by the food consumed. More specifically, the normal pH of saliva is 6.7 to 7.4, but when bacteria break down carbohydrates, the pH of saliva drops to 5.5, which is known as the critical pH value, and tooth caries are significantly accelerated at this level of pH.

Due to the importance of pH measurement, many endeavors have been done to measure pH effectively and efficiently. A relatively simple method of measuring pH can be performed using a pH test strip. In this method, a strip of litmus paper is immersed into a solution and the substance contained in the paper causes the paper to appear in a different color depending on the acidity level of the solution. The accuracy of this method, however, is low and highly dependent on human observation, and its applicability is limited to only one-time use. Conventional pH sensors with real-time measurement function consist of a glass membrane filled with a buffer. This type of pH sensor is relatively bulky and fragile. This means that the sensor can only be used in a location with sufficient surface area and can easily break when used in a pressurized environment.

In an attempt to eliminate the glass membrane in the conventional pH sensors, it has been proposed to use iridium oxide (IrOx) and silver chloride (AgCl) as the sensing and reference electrodes, respectively. To fabricate the IrOx electrode, the iridium (Ir) wire can be wetted with sodium hydroxide (NaOH) and heated to 800° C. in an electric furnace for 45 minutes. Accuracy of the electrode-based pH sensors, however, is dependent on peripheral temperature. Consequently, a thermistor has been integrated into the measurement platform to compensate for temperature, and the outputs of the measurement platform (e.g., amplitude and resonant frequency as a function of temperature and pH, respectively) were read via an interrogator coil. The proposed system is portable, but typically can only be read out via the coupled coils. Further, the use of AgCl makes the system fundamentally unappealing for biomedical applications, while biocompatibility is highly desirable.

Similarly, an Ir/IrOx sensing electrode has been used in conjunction with an Ag/AgCl reference electrode to measure tooth surface pH. It has been shown that the local pH values on the tooth surface with which the sensor was in direct contact are associated with caries status. Due to the physical aspects of the electrodes and the use of the non-biocompatible Ag/AgCl reference electrode, however, the measurement system can typically only be used for in vitro measurements, e.g., outside the body. In order to miniaturize the pH sensing system and provide the characteristic of deformability, the pH electrodes (e.g., IrOx and AgCl) have been fabricated on a polyimide substrate by a multi-step microfabrication process, e.g., e-beam evaporation, sol-gel process, lift-off, and sputtering. In this context, the fabricated pH sensor platform has a relatively small dimensions and is flexible, while the need for a complex microfabrication process directly affects the cost of the system and reduces its applicability as a disposal unit.

Furthermore, pH can be measured optically. The use of an optical pH sensor is a practical method for monitoring pH in real time and with biocompatibility in the in vivo environment. In this method, the cladding of the optical fiber is changed by applying a sensing film sensitive to pH ions. Thereafter, a light source, such as an LED, emits light through the fiber optic and the intensity of the light reflected from the sensing film, which can be measured by a photodetector or spectrometer, determines pH level. The versatility of such a measurement technique has been demonstrated for continuous measurement of pH in arterial blood and extracorporeal circulation. Although this method can be used for continuous pH measurement, the optical sensors usually require a bulky readout system, moreover, such a method may not be considered as a non-invasive measurement approach since the optical fibers are in contact with the solution and they have to be surgically placed in the artery.

In yet another method, a non-contact pH measurement using a high-quality factor microwave planner resonator has been proposed. In this method, it is shown that the effective permittivity of the resonator medium is a function of pH level, therefore different pH values lead to a change in the resonant frequency of the resonator. The system, however, requires an integrated fluidic channel above the resonator to transport the solution. As a result, the proposed system requires an additional fabrication process to integrate the fluid channel. The effective permittivity, however, is also a function of temperature and humidity. This means that the accuracy of the proposed non-contact pH measurement is relatively low, as environment temperature and humidity can fluctuate over time and affect the response of the pH sensor. Further, the moisture content in the oral cavity changes regularly, so the current method cannot be used to accurately measure pH in the mouth. Thus, current methods and systems for determining intraoral pH exhibit a number of limitations.

Therefore, there is a need for a system and method that can provide individualized care plan to patients by monitoring the pH value using an intraoral device placed within the oral cavity of the user. Also, the system should make feedbacks and/or recommendations based on plurality of health conditions of the user, specifically designed for each patient. Furthermore, the system should be easy to use and maintain.

SUMMARY

The present disclosure envisages an intraoral pH monitoring device. The intraoral monitoring device includes a flexible substrate, a plurality of sensors, which includes at least one pH sensor to generate an oral pH data, a rechargeable battery and a device module embedded within the intraoral device.

In one aspect of the present disclosure, an intraoral device for monitoring pH is disclosed. The device includes a flexible substrate, a plurality of sensors including at least one pH sensor, where the pH sensor generates an oral pH data. The device further includes a device module that receives the oral pH data from the at least one pH sensor and correlates the received oral pH data with one or more user related data to classify the oral pH data into one or more pre-defined categories indicative of at least one health condition. The user related data includes a pre-stored user data and/or a real-time generated user data. The device module further generates at least one or more feedback and/or recommendations for the user, based on the classification of the oral pH data into the one or more pre-defined categories, where the generated feedback and/or recommendations are appropriate to manage the at least one health condition. The oral pH data and/or the at least one or more feedback and/or recommendations are communicated to an external device that is communicatively coupled to the intraoral device.

In another aspect of the present disclosure, a method of monitoring pH using an intraoral pH is disclosed. According to the disclosed method, an oral pH data is received from at least one pH sensor embedded within the intraoral device by calculating the electric potential difference between a reference electrode and a sensing electrode placed within the sensor array. The oral pH data is then correlated with one or more user related data to classify the oral pH data into one or more pre-defined categories indicative of a health condition. Further, a machine learning module generates at least one or more feedback and/or recommendation for the user, based on the classification of the oral pH data into the one or more pre-defined categories, where the generated feedback and/or recommendations are appropriate to manage the at least one health condition. The oral pH data and/or the at least one or more feedback and/or recommendations are communicated to an external device which is communicatively coupled to the intraoral device.

In yet another aspect of the present disclosure, a system for monitoring intraoral pH is disclosed. The system includes an intraoral device, a docking station, a client device, a device management platform (DVMP), a data management platform (DMP), a remote monitor system (RMS) and a machine learning module. The intraoral device consists of a flexible substrate, a plurality of sensors which includes at least one pH sensor that receives the oral pH data. The DVMP is operatively coupled to the intraoral device to receive the oral pH data from the intraoral device. The DMP receives the oral pH data from the DVMP and correlates the oral pH data with one or more user related data. The docking station is configured to perform one or more functionalities for maintaining and interfacing with the intraoral device. The machine learning module is configured to analyse and classify the oral pH data into one or more pre-defined categories indicative of at least one health condition, where the machine learning module generates at least one feedback and/or recommendations related to the one or more health condition based on the analysis and classification of the oral pH data. The client device receives the oral pH data and/or at least one recommendation and/or feedback related to the one or more health conditions of the user. The intraoral device, docking station, client device, DVMP, DMP, RMS and the machine learning module are interconnectable in various ways such as via connectivity to a network and/or via direct device-to-device connectivity.

In an aspect, the intraoral device described herein is formed by using cyclic voltammetry process using a low temperature fabrication process.

In one aspect of the disclosure, the flexible substrate enables the intraoral device to take shape of the intra oral cavity of the wearer, which promotes contact between the sensors and the wearer's oral skin surface thereby enhancing the accuracy of measurement of the oral pH data. Further, the use of the flexible substrate allows designing and fabrication of a wide range of intraoral devices that can be used in wide applications, regardless of its geometry, due to the conformability of the design of the intraoral device.

In yet another aspect, the device module is configured to analyse the real time sensed data by using machine learning module by employing machine learning techniques such as Gradient boosted techniques, Decision tree techniques and Logistic regression techniques to evaluate emergency admission cases with prediction and analysis using Information Communication Technology (ICT) techniques.

In some aspects, the intraoral device described herein, the sensor array including the pH sensor further includes at least one sensing electrode, at least one reference electrode placed adjacent to each other such that the sensing electrode and the reference electrode are embedded on the flexible substrate and are placed equidistant from each other. The sensing electrodes are made from biocompatible material.

Advantageously, the one or more health conditions is selected from a group consisting of sleep related conditions, acidity reflux conditions, oral health conditions and so on.

BRIEF DESCRIPTION OF THE DRAWINGS

The above-mentioned implementations are further described herein with reference to the accompanying figures. It should be noted that the description and figures relate to exemplary implementations and should not be construed as a limitation to the present disclosure. It is also to be understood that various arrangements may be devised that, although not explicitly described or shown herein, embody the principles of the present disclosure. Moreover, all statements herein reciting principles, aspects, and embodiments of the present disclosure, as well as specific examples, are intended to encompass equivalents thereof.

FIG. 4 depicts an example implementation of the intraoral device placed within an oral cavity in accordance with implementations described herein.

FIG. 5 depicts an example implementation of the intraoral device placed within an oral cavity in accordance with implementations described herein.

FIG. 11 illustrates a method for intraoral pH monitoring in a patient, in accordance with one implementation of the present disclosure.

FIG. 12 illustrates an example method of monitoring pH using an intraoral device and providing feedback response based on the processed oral pH data, in accordance with one implementation of the present disclosure.

FIG. 14 depicts an example method for utilizing oral pH data obtained as part of intraoral monitoring in accordance with one or more implementations.

FIG. 15 depicts an example method for intraoral monitoring in accordance with one or more implementations.

FIG. 16 depicts an example method for security attributes as part of intraoral monitoring in accordance with one or more implementations.

FIG. 17 illustrates an example system that includes an example computing device that is representative of one or more computing systems and/or devices that are usable to implement the various techniques described herein.

DETAILED DESCRIPTION

Figure 1:
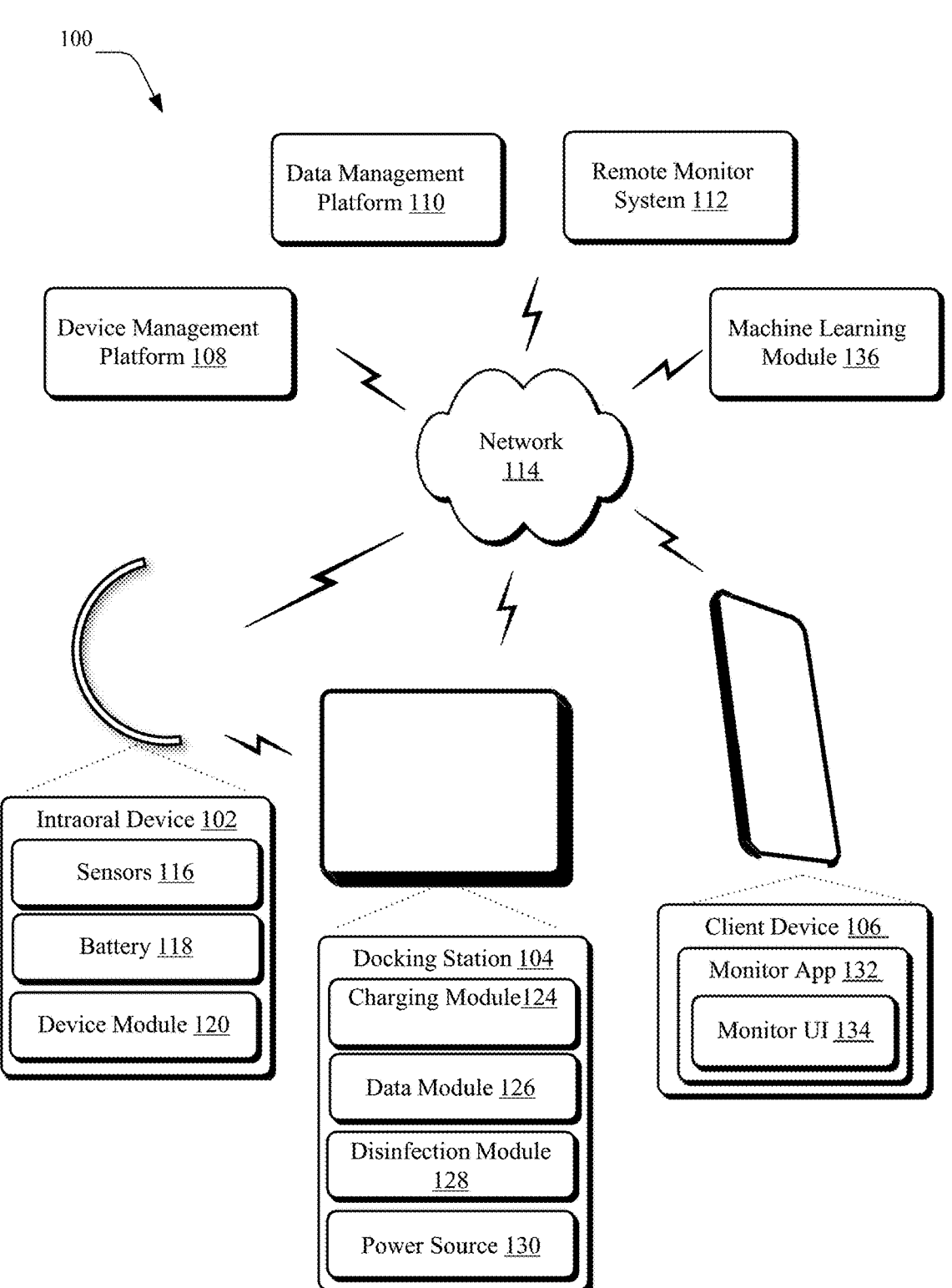
FIG. 1 is an illustration of an environment depicting example implementation of systems and methods for intraoral pH monitoring as described herein.

Embodiments, of the present disclosure, will now be described with reference to the accompanying drawing.

In the following description, certain specific details are set forth in order to provide a thorough understanding of various disclosed embodiments. However, one skilled in the relevant art will recognize that embodiments may be practiced without one or more of these specific details, or with other methods, components, materials, etc.

Unless the context indicates otherwise, throughout the specification and claims which follow, the word "comprises" and variations thereof, such as, "comprises" and "comprising" are to be construed in an open, inclusive sense that is as "including, but not limited to." Further, the terms "first," "second," and similar indicators of the sequence are to be construed as interchangeable unless the context clearly dictates otherwise.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

Overview

To overcome the challenges of pH monitoring presented in conventional systems, systems and methods for intraoral pH monitoring is described. In implementations, monitoring variations in the pH of aqueous solutions provides important information, such as for industrial and medical applications. For instance, it has been shown that saliva pH can be used as a biomarker to determine the health status of individuals. Accordingly, this disclosure describes non-invasive systems and methods for monitoring pH in the oral cavity with the ability to measure in real time and continuously.

For instance, the described system provides a single or a group of reference electrodes made of platinum and/or a single or a group of sensing electrodes made of iridium oxide. The described electrodes and their associated readout circuits can be positioned on a flexible substrate, and thus the physical shape of the monitoring system can be adjusted according to the curvature of the oral cavity. According to implementations, the electrical potential difference between the reference electrode(s) and the sensing electrode(s), which is produced by contact with saliva, is a function of the pH value. Further, a trained machine learning model can be used to analyze and classify the health status of individuals based on the plurality of health conditions. The plurality of health conditions may include sleep related conditions, acidity reflux conditions, oral health related conditions and so on. Thus, the systems and methods for intraoral pH monitoring described herein address the aforementioned drawbacks exhibited in current techniques.

The pH sensor represents functionalities for measuring the pH (e.g., relative acidity or alkalinity) within an oral cavity. The pH sensor, for instance, continuously measures the pH level of the oral cavity, e.g., saliva pH. The oral pH data from the pH sensor can be utilized for various purposes. For instance, a normal pH range for saliva is 6.2 to 7.6. Further, intraoral pH can decrease slowly over a sleep session, while sleeping with breathing via the oral cavity can result in a further decrease in pH over a longer period of time. Thus, measured pH levels can be used to identify breathing routes and incorporated with other sensor outputs to accurately determine sleep stages.

In the present disclosure, various types of users are described that can participate in aspects of systems and methods for intraoral pH monitoring. The following are examples of such users:

1) Unique User—a consenting individual assigned and confirmed to an instance of an intraoral device. A unique user, for instance, may share, assign access, allow other users (e.g., permissive users, clinicians, organizations, third parties, etc.) to access, evaluate, share, view, and/or distribute information collected, processed, and analyzed according to the described techniques.

2) Permissive User—a consenting individual, application, program, organization, and/or platform assigned, permitted by a user (e.g., a unique user) to access data collected by an intraoral device.

3) Clinician(s)—a consenting party, or parties, indicated for access to user data in order to view, evaluate, and/or manage the accessed data for purposes including but not limited to ensuring usage and compliance, therapeutic efficaciousness, disease management and improvement, monitoring behavior(s) related to sleep and wake, productive analysis, and/or other purpose related to health and wellness of a user of an intraoral device. A clinician may interact with a user in various ways, such as in-person and/or remotely via an approved application and/or platform and in a secure manner.

4) Third Parties—a consenting party, or parties, indicated for access to user data in order to view, evaluate, and/or manage the accessed data for purposes including but not limited to ensuring usage and compliance, therapeutic efficaciousness, disease management and improvement, monitoring behavior(s) related to sleep and wake, productive analysis, and/or other purpose related to health and wellness of a user of an intraoral device. A third party may interact with a user in various ways, such as in-person and/or remotely via an approved application and/or platform and in a secure manner.

Example Environment

FIG. 1 is an illustration of an environment 100 in an example implementation that is operable to employ systems and methods for intraoral pH monitoring as described herein. The environment 100 includes an intraoral device 102, a docking station 104, a client device 106, a device management platform (DVMP) 108, a data management platform (DMP) 110, a remote monitor system (RMS) 112 and a machine learning module 136. According to various implementations, the intraoral device 102, docking station 104, client device 106, DVMP 108, DMP 110, RMS 112 and the machine learning module 136 are interconnectable in various ways further to implementations described herein, such as via connectivity to a network 114 and/or via direct device-to-device connectivity. The network 114 can be implemented in various ways, such as a wireless network, a wired network, and/or a combination of wired and wireless networks and is implemented via any suitable architecture. Examples of the network 114 include the internet, a wide area network (WAN), a local area network (LAN), a mesh network, and combinations thereof.

Examples of devices that are used to implement the docking station 104, client device 106, DVMP 108, DMP 110, RMS 112 and machine learning module 136 includes a desktop computer, a laptop computer, a mobile device (e.g., assuming a handheld configuration such as a tablet or mobile phone), a server device, and so forth. Additionally, the client device 106, DVMP 108, DMP 110, RMS 112 and machine learning module 136 are implementable using a plurality of different devices, such as multiple servers utilized by an enterprise to perform operations "over the cloud" as further described in relation to FIG. 17.

The intraoral device 102 includes plurality of sensors 116, out of which one is at least a pH sensor which is configured to be positioned within an oral cavity and generates oral pH data. The sensors 116, for instance, include electrodes that can be used to measure electrical properties within an intraoral cavity, such as electrical potential differences between different instances of the sensors 116. It should be noted that the plurality of sensors includes one or more of pH sensor, PPG, accelerometer, acoustic sensor, and so on. The data obtained by intraoral pH sensor in conjunction with other biological data collected from the mouth via PPG or accelerometer can significantly enhance the accuracy of identifying sleep or other disorders.

The intraoral device 102 also includes a rechargeable battery 118 and a device module 120. The rechargeable battery 118 represents a power source 130 for the intraoral device 102 and can be implemented in various ways, such as a single battery, a battery array, and so forth. The device module 120 represents functionality for performing various tasks for the intraoral device 102, such data management for the intraoral device 102, e.g., receiving oral pH data from the sensors 116, storing oral pH data, communicating the oral pH data received by the intraoral device 102 to other entities, analysing oral pH data, communicating data to the intraoral device (e.g., for configuring operation of the intraoral device 102), communicating the feedback and/or recommendations generated by the machine learning module 136 to the external device and/or user and so forth. In implementations the device module 120 includes circuitry such as an application-specific integrated circuit (ASIC), a field-programmable gate array (FPGA), and/or other processing and data storage functionality. The device module 120 can be implemented as one or more microprocessors, microcomputers, microcontrollers, digital signal processors, central processing units, state machines, logic circuitries, and/or any devices that manipulate signals based on operational instructions.

The device module 120 also represents functionality for enabling data communication from and to the intraoral device 102. The device module 120, for instance, can utilize different wireless and/or wired communication protocols, such as Bluetooth™, Near-field communication (NFC), ZigBee, and so forth. In at least one implementation the device module 120 includes functionality for enabling charging of the battery 118, such as for implementations where the battery 118 is rechargeable. Alternatively, the battery 118 can be implemented as a single-use battery.

The docking station 104 is configured to perform various functionalities for maintaining and interfacing with the intraoral device 102. The docking station 104, for instance, includes a charging module 124, a data module 126, a disinfection module 128, and a power source 130. The charging module 124 represents functionality for charging a power supply (e.g., rechargeable battery) of the intraoral device 102. The data module 126 represents functionality for transferring data from and/or to the intraoral device 102, such as to various other functionality of the environment 100. The disinfection module 128 represents functionality for disinfecting and/or drying the intraoral device 102.

The client device 106 is configured to connect to the docking station 104 and/or the intraoral device 102 to provide various user functionalities. For instance, the client device 106 includes a monitor application ("app") 132 that implements a monitor user interface 143 such as a graphical user interface (GUI). According to various implementations, the monitor app 132 receives data that is measured and analyzed by the intraoral device 102, such as oral pH data from various sensors that is generated by and/or stored on the intraoral device 102. Further, the monitor app 132 can enable data transfer to the intraoral device 102, such as for configuring (e.g., updating and/or repairing) functionality of the intraoral device 102.

In at least some implementations, the monitor app 132 represents a downloadable interface such as for sending and receiving user data throughout the present system. For instance, the monitor app 132 can receive data from the intraoral device (e.g., directly and/or via the docking station 104) and transmit the data to the DVMP 108 and/or the RMS 112. Further, the monitor app 132 can receive data from the DVMP 108 and/or the RMS 112. Utilizing the monitor app 132, users can view and share data, including outside the present system in a number of categories, including but not limited to permissive users, other users of the present system, applications, platforms, clinicians, organizations, and so forth. Unique users, for instance, give the present system initial consent to collect data via the monitor app 132, and after this consent the present system initiates data collection.

The DVMP 108, the DMP 110, the RMS 112 and the machine learning module 136 represent functionality for performing various functionality for systems and methods for intraoral pH monitoring described herein. For instance, the DVMP 108 represents functionality for brokering data transfer between different entities of the environment 100 and/or for performing processing of data received from the client device 106, e.g., oral pH data generated at the intraoral device 102. The DVMP 108, for instance, can receive data from the monitor app 132 and communicate the data to the DMP 110 and/or the RMS 112. Further, the DVMP 108 can receive data from the DMP 110 and/or the RMS 112 and communicate the data to the monitor app 132.

The DMP 110 represents functionality for data aggregation (e.g., oral pH data), data analysis via algorithms and other proprietary methods, report generating, data sharing, implementing machine learning attributes, data storage, and so forth. The DMP 110 also provides integration with applications, platforms, and application program interfaces (API) as well service providers such as electronic health records (EHR) systems, and blockchain systems.

Example functionalities that may be implemented individually and/or cooperatively by the DVMP 108 and the DMP 110 include:

(1) Data sharing with permissive users with appropriate permissions, data analysis using algorithms, and machine learning tasks;

(2) Responding to queries from various entities;

(3) Securing interaction with application programming interfaces (API) for approved and authorized purposes;

(4) Secure authentication for the users with appropriate permissions, such as permissive users;

(5) Ordering user data for data analysis of user data, such as nightly, weekly, monthly, and other.

(6) Executing machine learning algorithms and presenting results in accordance with user requests, such as for unique users, permissive users, clinicians, third parties, and so forth.

(7) Sending and receiving user data in encryption (8) Exacting insights from data or lack of data from a user. Some examples include patterns in usage, changes in health-related condition (acidity reflux, GERD, sleep related issue, oral health issues and others) relative to the unique user. These insights may be used by permissive users for clinical purposes, such as to improve health outcomes.

(9) Express critical values related to health-related condition (such as described above) in a manner customizable by a user for the purpose of alerts, reporting, population health comparison, titration levels of the intraoral device 102, and so forth.

The RMS 112 represents functionality for data analysis via machine learning algorithms and machine learning models, report generating, data sharing, data storage, and so forth. The RMS 112 can implement a cloud-based web application accessible by permissive users, clinicians, organizations, third parties, and so forth. For instance, permissive users can interact with the RMS 112 to view, evaluate, manage, and analyze user data such as for disease management, therapeutic adherence, and efficacy, e.g., via reporting and testing measures. In at least some implementations, the RMS 112 can enable the diagnosis and treatment of different disorders by collecting patient health data sourced by the intraoral device 102 and allowing a provider (e.g., clinic, doctor office, etc.) to monitor the health data and provide feedback and/or recommendations to the patient based upon the results by classifying the result of the oral pH data based on plurality of health conditions. The plurality of health conditions includes sleep related condition, acidity reflux condition, oral health related condition and so on.

The RMS 112, for instance, enables remote patient monitoring where a patient and a practitioner may be locationally remote from one another and data obtained from an intraoral device 102 installed in a user is processed and provided to the RMS 112, where a practitioner may access and analyze the data from any suitable location. Also, the feedback and/or associated recommendations are provided to the user by the remote clinician, doctor etc. whenever needed. For instance, if the oral pH data obtained are above the threshold value, then the user is provided feedback and/or recommendation in the form of some diet related suggestion, some sleep position related suggestion, changes in the medication and the treatment plan if the condition is severe and so on.

Accordingly, data received from the intraoral device 102 can be propagated (e.g., transmitted and communicated) across the environment 100 and utilized by the various described entities for various purposes. According to various implementations, appropriate data security protocols are observed as part of collecting and maintaining data in the environment 100 and for the life of the data within the environment 100. Examples of different data handling protocols are described below.

The environment 100 further includes a machine learning module 136, which represents functionality for performing analysis on various data received by the intraoral device 102. While the machine learning module 136 is illustrated separately from other entities of the environment 100, it is to be appreciated that the machine learning module 136 can be implemented as functionality of one or more of the described entities, such as the client device 106, the DVMP 108, the DMP 110, and/or the RMS 112. According to implementations, the machine learning module 136 can implement different machine learning and/or artificial intelligence methods (e.g., deep learning, neural networks, Q-learning, etc.) to correlate oral pH data, analyse and classify it accordingly into one or more pre-defined categories indicative of at least one health condition.

The machine learning module 136 analyzes the received oral pH data and classifies it into one or more pre-defined categories indicative of at least one health condition, where the user related data includes a pre-stored user data and/or a real-time generated user data. These health conditions may include sleep related conditions, acidity reflux conditions, oral health conditions and so on. Based on the classified oral pH data the feedbacks and/or recommendations are generated and communicated to the user based on the past data record of the user stored in the machine learning module 136, received oral pH data (for instance, checking the severity of any disease or condition based on the oral pH data) and so on. The feedback and/or recommendations can also be provided by comparing the medical records of other patients with similar conditions. The record of other patients and the feedback and/or recommendations given to them during that time gets stored in the machine learning module 136. For instance, if a user has severe acidity due to sleep apnea, the pH sensor will receive the oral pH data and will correlate the oral pH data along with the user related data to classify the oral pH data into one or more pre-defined categories indicative of at least one health condition, where the user related data includes a pre-stored user data and/or a real-time generated user data. The user related data may include user details like user ID, contact details, device details, health related information etc. The correlated oral pH data is classified using machine learning module 136 and the result is compared with the threshold values to check the severity of the condition (acidic reflux in this example). For instance, the machine learning module 136 may classify and pre-define a threshold value of oral pH data. If it is between 5-7, then the pH range is normal and the users do not have any health issue, if it is greater than 7 or below 4 then the users have severe health conditions. Based on the severity of the acidic reflux condition, the machine learning module 136 may recommend the user to "eat curd", as it was helpful for another patient with the same symptoms. The machine learning module 136 can also predict future health related conditions by tracking the past records of the user and can notify them in advance to take necessary precautions in order to avoid such health condition.

Figure 2:
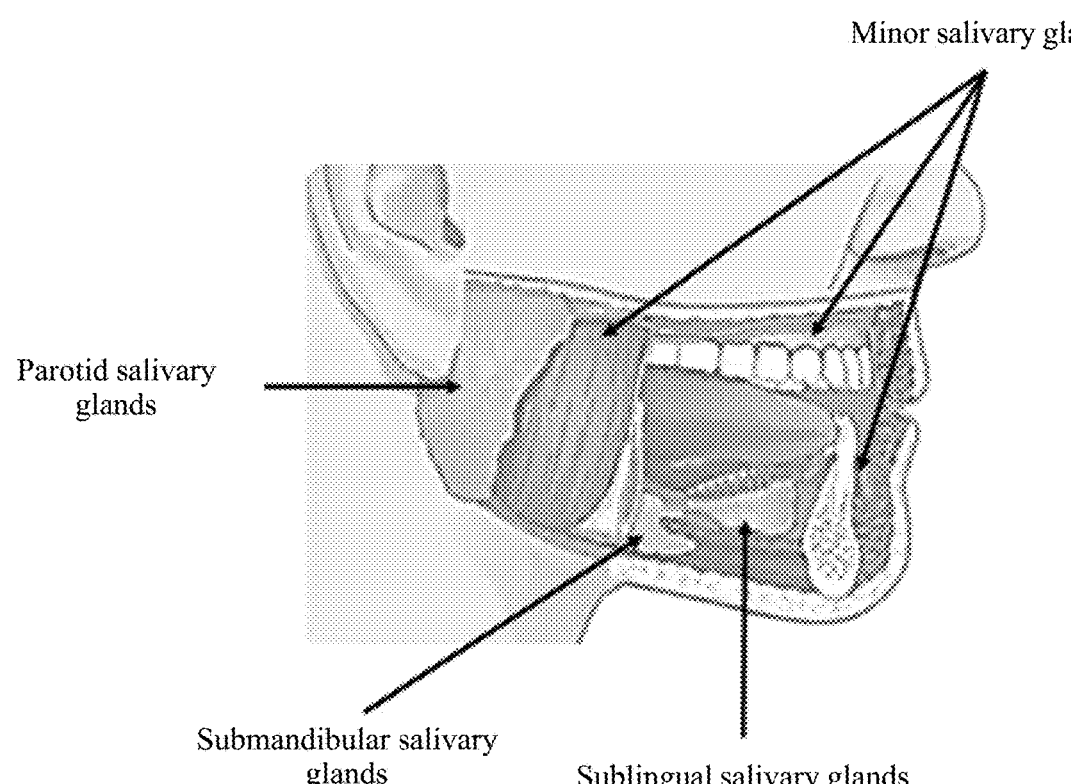
FIG. 2 depicts the anatomy of the salivary glands in the oral cavity.

FIG. 2 depicts the anatomy 200 of the salivary glands in the oral cavity. According to FIG. 2, saliva is produced by a group of glands located in different parts of the mouth. For example, the parotid glands, located just in front of the ears, produce 20% of the salivary flow, and this percentage can be increased to as much as 60% when stimulated. The submandibular salivary glands, located below the jaw, produce about 65% of the salivary flow. The salivary glands at the base of the mouth on either side of the tongue, called the sublingual salivary glands, produce about 5-7% of the unstimulated salivary flow. Minor salivary glands located in the lips and buccal mucosa are responsible for 8-10% of the salivary flow. It can be deduced from this that the majority of saliva flow is produced at the back of the oral cavity. Consequently, the back of the oral cavity is a suitable anatomical position to place the sensors 116 (e.g., reference and sensing electrodes) of the intraoral device 102.

Figure 3:
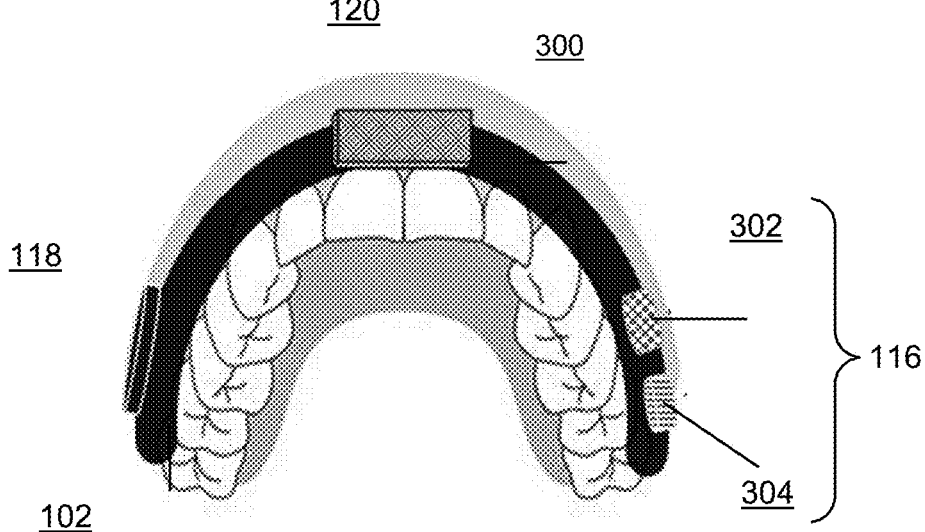
FIG. 3 depicts an example implementation of the intraoral device placed within an oral cavity in accordance with implementations described herein.

FIG. 3 depicts an example implementation of the intraoral device 102 placed within an oral cavity in accordance with implementations described herein. In this particular implementation the intraoral device 102 is placed on the upper jaw (maxilla) with components of the intraoral device 102 facing the lips, i.e., not the gums. The intraoral device 102, for instance, includes a substrate 300 with the sensors 116, the battery 118, and the device module 120 attached to (e.g., embedded within) the substrate 300.

The substrate 300 may be formed from any suitable material that enables placement of the various components of the intraoral device 102 as well as positioning of the intraoral device 102. The substrate 300, for instance, is formed from a flexible material such as Kapton™ tape, a flexible polymer (e.g., polyamide), and/or other flexible material. In at least one implementation, electrical connection between the various components of the intraoral device 102 on the substrate 300 can be implemented in various ways, such as using silver ink. The use of the flexible substrate 300 is advantageous such as to enable the intraoral device 102 to be curved according to the curvature of a wearer. Further, the use of the flexible substrate 300 enables the intraoral device 102 to be designed and fabricated and then attached to a wide range of oral appliances, regardless of their geometry, due to the conformability of the design of the intraoral device 102.

The sensors 116 includes a sensing electrode 302 and a reference electrode 304 that are each configured to measure a respective voltage value when placed within an oral cavity. As further detailed below, the device module 120 can utilize voltage values detected by the sensing electrode 302 and the reference electrode 304 to determine a pH within an intraoral cavity, such as based on an electrical potential difference between voltage values detected by the sensing electrode 302 and the reference electrode 304, respectively. In at least some implementations, the sensing electrode 302 is formed using biocompatible material like iridium (Jr) and/or Jr oxide (IrOx) or Antimony (Sb). Further, the reference electrode may be formed using platinum (Pt).

According to implementations, the device module 120 can receive oral pH data such as based on voltage values generated by the sensing electrode 302 and the reference electrode 304 and can utilize the oral pH data in various ways, such as to perform local processing and/or transmit the data to other entities, such as the client device 106, the DVMP 108, the DMP 110, the RMS 112 and/or the machine learning module 136.

FIG. 4 depicts an example implementation 400 of the intraoral device 102 placed within an oral cavity in accordance with implementations described herein. In this particular implementation the intraoral device 102 is placed on the lower jaw (mandible) with components of the intraoral device 102 facing the lips, i.e., not the gums. The intraoral device 102, for instance, includes the substrate 300 with the sensors 116, the battery 118, and the device module 120 attached to (e.g., embedded within) the substrate 300. Further, the sensors 116 include the sensing electrode 302 and the reference electrode 304.

FIG. 5 depicts an example implementation 500 of the intraoral device 102 placed within an oral cavity in accordance with implementations described herein. In this particular example, the intraoral device 102 can be placed either on the upper jaw or on the lower jaw at the posterior of the teeth, with the sensing electrode 302 and the reference electrode 304 facing the tongue. Accordingly, this positions the sensing electrode 302 and the reference electrode 304 in a location close to the back of the oral cavity which takes advantage of the high salivary flo w at this anatomical position. The intraoral device 102 includes the substrate 300 with the sensing electrode 302 and the reference electrode 304, the battery 118, and the device module 120 attached to (e.g., embedded within) the substrate 300.

Figure 6:
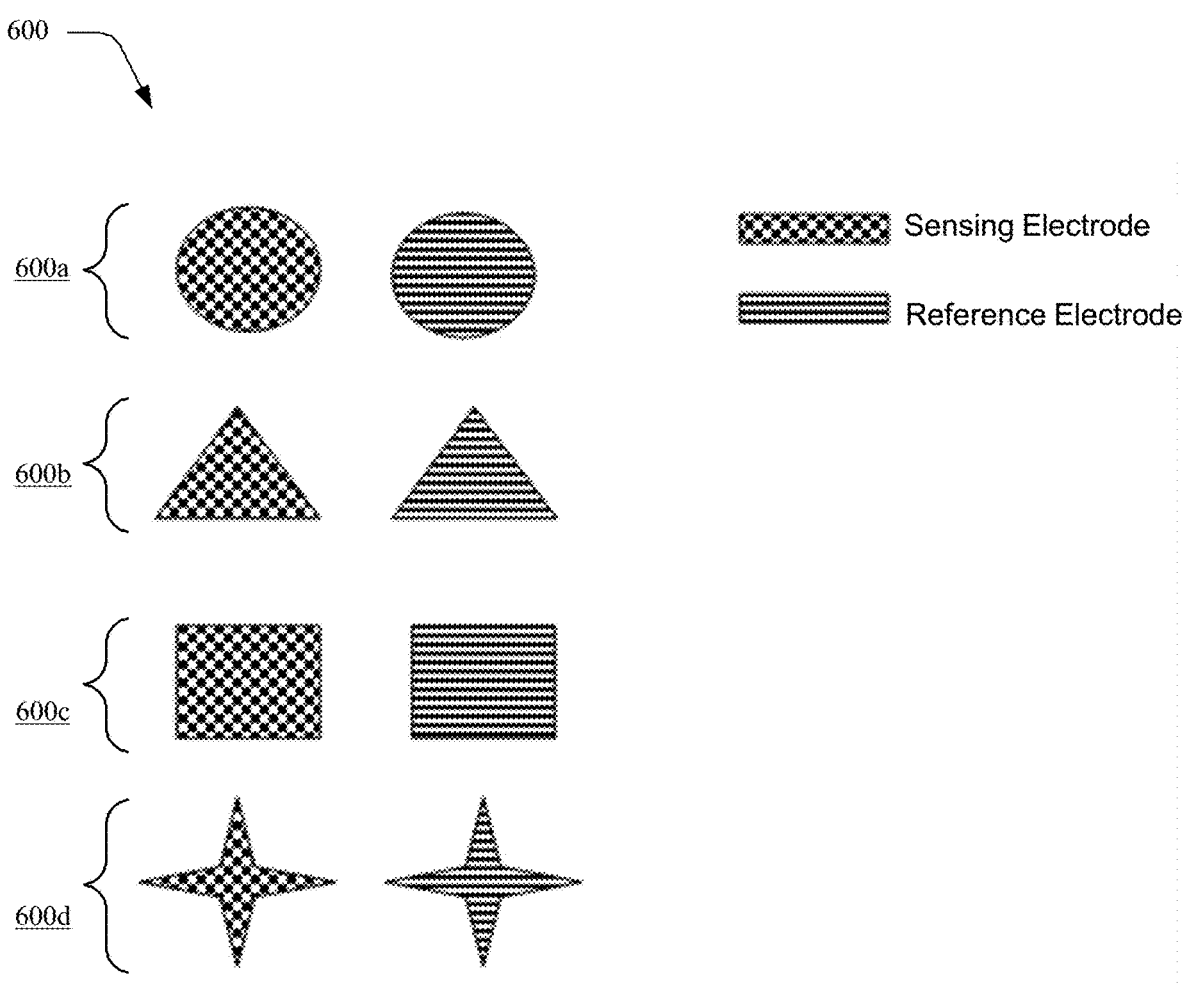
FIG. 6 depicts different topologies that can be used to form and/or shape the different sensors, such as the sensing electrode and/or the reference electrode.

FIG. 6 depicts different topologies 600 that can be used to form and/or shape the different sensors 116, such as the sensing electrode 302 and/or the reference electrode 304. The topologies 600 include a topology 600a (e.g., circular), a topology 600b (e.g., triangular), a topology 600c (e.g., square), and a topology 600d, e.g., star-shaped.

According to implementations, topology can affect the accuracy of the pH measurement. For instance, depending on the anatomical position of the sensing electrode 302 and reference electrodes 304 in the oral cavity (e.g., maxilla, mandible, anterior or posterior teeth), an optimal topology for the electrodes will be chosen to maximize the accuracy of the measurement. It should be noted that the sensing electrodes 302 and reference electrodes 304 can have various combinations of the shapes shown in FIG. 6. For example, the sensing electrode 302 can be circular, while the reference electrode 304 can have a star-shaped structure, and vice versa. Use of the different shapes for sensing electrode 302 and reference electrode 304, for instance, increases the contact area between the electrodes and saliva, which can ultimately lead to an increase in the sensitivity of the pH monitoring system.

Figure 7:
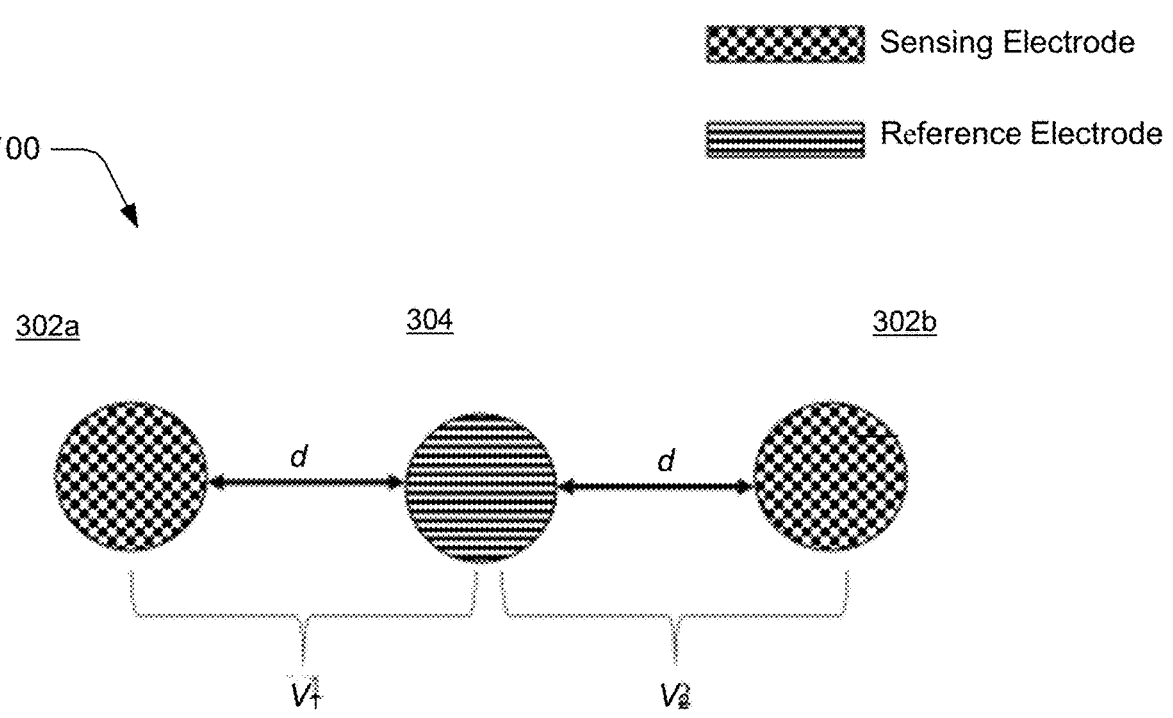
FIG. 7 depicts a sensor array in accordance with one or more implementations.

FIG. 7 depicts a sensor array 700 in accordance with one or more implementations. The sensor array 700, for instance, represents at least one implementation of the sensors 116. In this particular example, the sensor array 700 includes a sensing electrode 302a, a sensing electrode 302b, and a reference electrode 304. In at least some implementations, the sensor array 700 further increases the sensitivity and reliability of pH measurement from the oral cavity by the intraoral device 102.

Differential measurement, for instance, is a viable method to minimize the effects of sudden environmental changes on the actual measurement parameters. Therefore, the electrodes of the intraoral device 102 described in this document can be implemented in the form of differential measurement, such as shown with regard to the sensor array 700. In the sensor array 700, the sensing electrodes 302a, 302b (collectively 302) are positioned on the intraoral device 102 at an approximately equal distance (d) from the reference electrode 304. A measured difference electrical potential between the sensing electrode 302a (Vi) and the sensing electrode 302b (V 2) with respect to the reference electrode 304 therefore can indicate a pH value. Using the sensor array 700, for instance, mitigates undesirable environmental changes on the measured pH.

As mentioned above, Ir/IrOx can be used as a sensing electrode 302 in the intraoral device 102. For instance, Jr metal can be used by growing a thin oxide layer on its surface. This type of material (i.e., IrOx) is biocompatible and can be produced using a relatively simple low temperature manufacturing process.

One possible approach to deposit oxides on the surface of Jr metals and to fabricate Ir/IrOx electrodes is cyclic voltammetry. In this electrochemical method, three electrodes, namely a working electrode, a reference electrode, and a counter electrode, are immersed in an electrolyte solution, and then the electric potential between the working and reference electrodes is linearly swept by a potentiostat. At the same time, a current change between the working and counter electrodes is measured. In this setup for developing Ir/IrOx, pure Jr metal can be used as the working electrode, while reference and counter electrodes can be silver (Ag) and or silver chloride (AgCl), and Pt, respectively. Sulfuric acid can be used as the required electrolyte solution.

Figure 8:
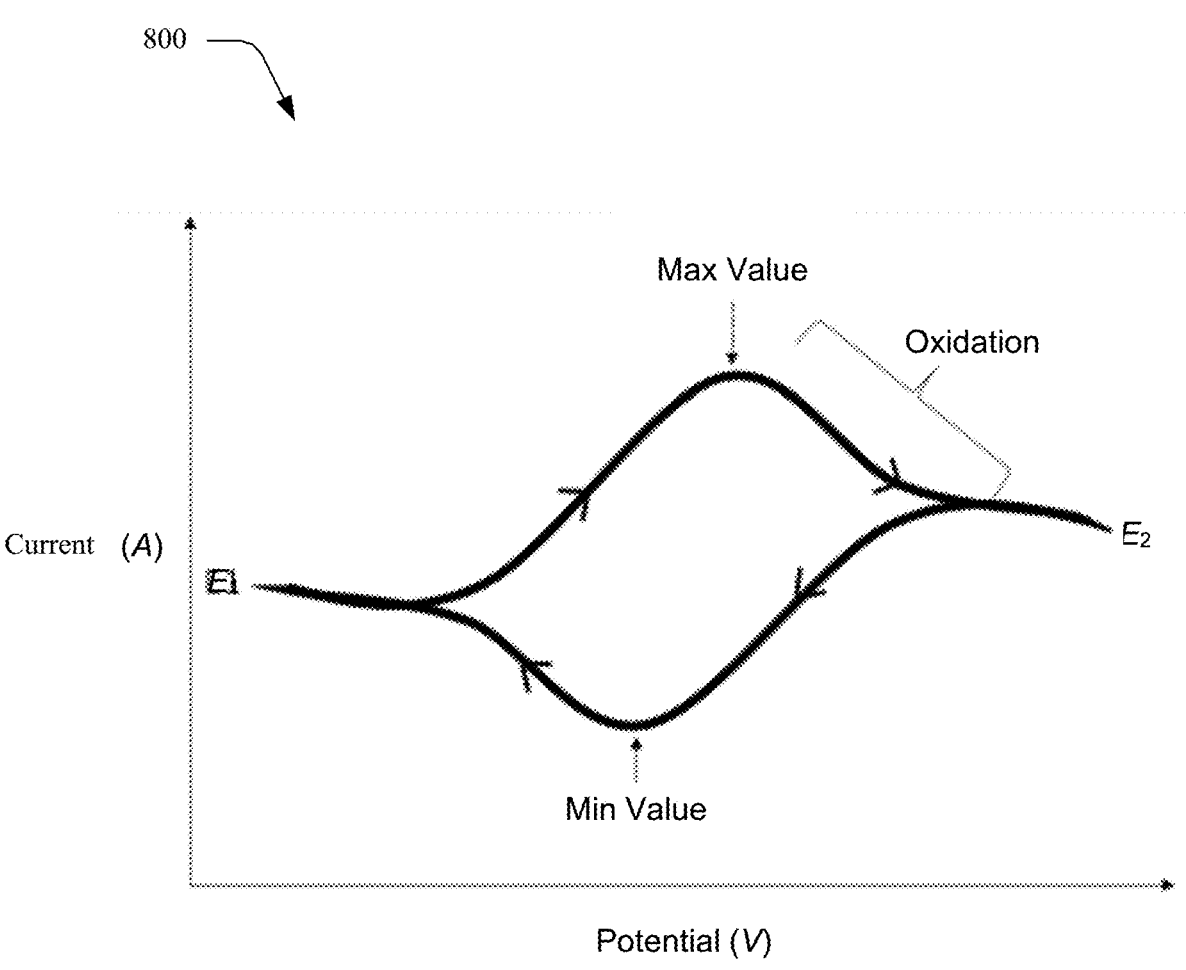
FIG. 8 depicts a diagram obtained from cyclic voltammetry of Ir, referred to as cyclic voltammogram.

FIG. 8 depicts a diagram 800 obtained from cyclic voltammetry of Jr, referred to as cyclic voltammogram. As can be seen, the electric potential is swept from E1 to E2 and vice versa, and the current between Jr and Pt electrodes is measured in real time. In this diagram, oxidation of Jr can be seen when the peak current gradually decreases until the last input voltage, E2.

Figure 9:
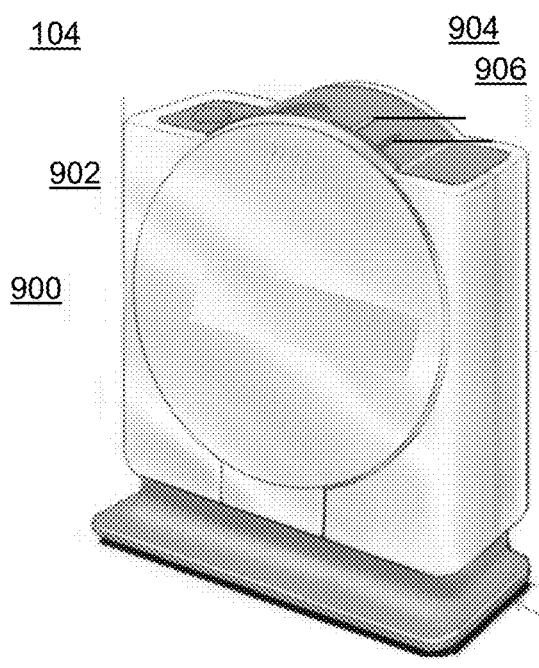
FIG. 9 depicts an example implementation of the docking station in accordance with implementations described herein.

FIG. 9a depicts an example implementation of the docking station 104 in accordance with implementations described herein. In FIG. 9a, the docking station 104 is depicted in a closed position, such as with the intraoral device 102 positioned within an interior cavity of the docking station 104 for charging the battery 118, disinfection of the intraoral device 102, data transfer from and/or to the intraoral device 102, and so forth. The docking station 104 includes a housing 900, a hinged door 902, a battery status indicator 904, and a disinfection status indicator 906. The door 902 is hingeably attached to the housing 900 to enable the door 902 to be opened and closed relative to the housing 900 for insertion and removal of the intraoral device 102 relative to the docking station 104. The battery status indicator 904 is operable to indicate a charging status of the battery 118 of the intraoral device 102. The battery status indicator 904, for instance, represents a light (e.g., LED light) that can be illuminated with different colors or frequencies that represent different charging status of the battery 118. The disinfection status indicator 906 is operable to indicate a disinfection status of the intraoral device 102. The disinfection status indicator 906, for instance, represents a light (e.g., LED light) that can be illuminated with different colors that represent different disinfection status of the intraoral device 102, such as whether a preset disinfection cycled of the docking station 104 is in progress or complete.

Figure 10:
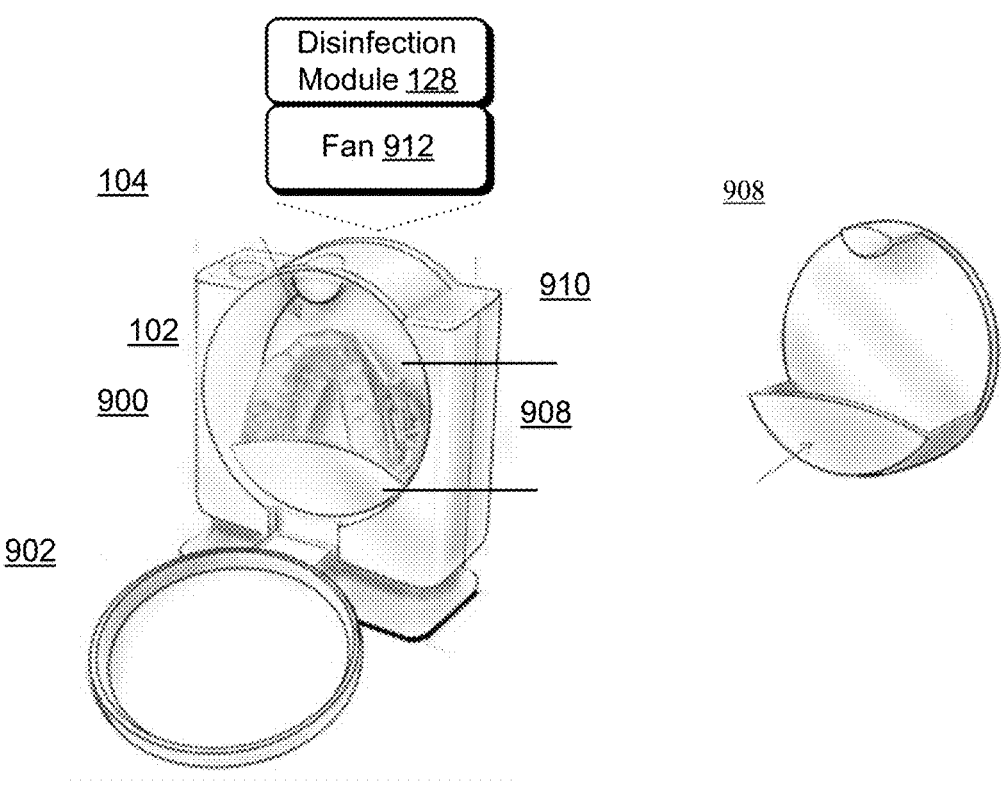
FIG. 10 depicts the docking station with the door in an open position relative to the housing.

FIG. 10 depicts the docking station 104 with the door 902 in an open position relative to the housing 900. The intraoral device 102 is positioned within a tray 908 positioned within a cavity 910 in the housing 900. Also positioned within the cavity 910 are the disinfection module 128 and a fan 912. The disinfection module 128, for instance, includes a UV light positioned to project UV light waves onto the intraoral device 102 for purpose of disinfecting the intraoral device 102. The fan 912 can circulate air within the cavity 910 to dry the intraoral device 102. FIG. 10 also depicts the tray 908 removed from the housing 900 of the docking station 104. Removal of the tray 908 enables cleaning, maintenance, and replacement of the tray 908.

FIG. 11 illustrates a method 1100 for intraoral pH monitoring in a user, in accordance with one implementation of the present disclosure.

The method 1100, for instance, is performed at least in part in the context of the environment 100. The method 1100 for intraoral pH monitoring in a user includes:

Step 1102 involves receiving an oral pH data from at least one pH sensor116 embedded within the intraoral device 102 by calculating the electric potential difference between a reference electrode 304 and a sensing electrode 302 placed within the sensor array 700.

Step 1104 involves correlating the oral pH data with one or more user related data to classify the oral pH data into one or more pre-defined categories indicative of a health condition. The user related data may include device details, user ID, date, time, user health details and so on.

Step 1106 involves generating, at least one or more feedback and/or recommendation for the user using a machine learning model 136, based on the classification of the oral pH data into the one or more pre-defined categories, wherein the generated feedback and/or recommendation is appropriate to manage the at least one health condition. For instance, the plurality of health conditions may include sleep related conditions, acidity reflux conditions, oral health related conditions and so on.

Step 1108 involves communicating the oral pH data and/or at least one recommendation and/or feedback from the intraoral device 102 to an external device and/or person via a wireless and/or wired data transmission.

Recommendations can also be made using machine learning module 136 by comparing the oral pH data of the user with the other patient's data dealing with the same situation and symptoms. For instance, a patient is suffering from severe acidic reflux condition during sleep apnea or other sleep related conditions and in order to prevent it he/she took curd, which helped the user to cure acidic reflux condition. This will get stored in the machine learning module 136. Whenever any other user with the similar health condition will face the same issue, the oral pH data of the user will be received and analysed. After analysis, if the symptoms and conditions of both the users are found to be the same, then the machine learning module 136 will communicate the same "eat curd" as a recommendation to the second user.

The method of monitoring pH of an intraoral device 102, uses a device module 120 which is configured to process the real time sensed data by using a machine learning module 136 and employing machine learning techniques like Gradient boosted techniques, Decision tree techniques and Logistic regression techniques to receive and store the data corresponding to the oral pH data associated with the respective users and is further configured to classify the oral pH data corresponding to the plurality of health conditions associated with said user using Information Communication Technology (ICT) techniques.

The method of monitoring pH of an intraoral device 102 communicates the oral pH data that may be encoded and/or encrypted for data security. Further, the method uses blockchain techniques as part of user data storage, transfer, and access, which can improve data security, privacy, and data accessibility of various users.

In at least one implementation, the device module 120 is configured to employ energy efficient FoG based Internet of Things (IoT) network techniques to monitor intraoral pH. In another embodiment, the controller can be implemented as one or more microprocessors, microcomputers, microcontrollers, digital signal processors, central processing units, state machines, logic circuitries, and/or any devices that manipulate signals based on operational instructions.

Further, the communication of the oral pH data and feedback and/or recommendations is done to transmit the data to the cloud based remote server for historical data storage and monitoring log via a network 114. In an embodiment, the network 114 may include the Internet, wireless network, wired network, one or more telecommunications networks (e.g., Public Switched Telephone Networks (PSTNs)), a wired or wireless network, a wireless area network, a Wireless Video Are Network (WVAN), a Local Area Network (LAN), a WLAN, a PAN, a WPAN, WANs, metropolitan area networks (MANs), or an intranet.

FIG. 12 illustrates an example method 1200 of monitoring pH using an intraoral device and providing feedback response based on the processed oral pH data, in accordance with one implementation of the present disclosure.

The exemplary method 1200, for instance, is performed at least in part in the context of the environment 100. As shown previously in FIG. 1, the intraoral device 102 is placed within the oral cavity of the user 1202. Further, an oral pH data is received from a pH sensor placed within an intraoral device 102, at 1204. The device module (120 of FIG. 1), for instance, receives oral pH data from the sensors (116 of FIG. 1). Further, at step 1206, oral pH data is correlated with other user related data to classify the oral pH data into one or more pre-defined categories indicative of a health condition. The user related data may include user id, date, time, user health related details, device details and so on. The device module 120, for instance, correlates the oral pH data along with the user related data.

At step 1208, the oral pH data is classified into a pre-defined category based on plurality of health conditions. These health conditions include sleep related conditions 1208a, acidity reflux conditions 1208b, non-acidic reflux conditions 1208c and others 1208d. The other health conditions 1208d may include oral health related conditions, tooth decay related conditions and so on. The machine learning module 136 performs the process of classification of the oral pH data.

Step 1210 generates feedback based on the classified oral pH data analyzed in the Step 1208. For instance, the user 1202 is suffering from sleep apnea or other sleep related issues and is facing acidity reflux conditions 1208b during sleep. During the case of acidity conditions 1208b during the sleep, the pH sensor placed inside the oral cavity of the user 1202 will detect the change in the pH level and start receiving the oral pH data as shown in Step 1204. The machine learning module 136 will generate feedback, which may be in the form of notification to the third-party application 132 or a direct communication to the user 1202 or physician or any other healthcare professional. The feedback is provided to the user 1202 that "acidic reflux conditions are monitored due to change in the pH value". Based on the provided feedback, the user 1202 may consult his/her physician or may take any other precautions or medications based on the severity of the acidity reflux conditions 1208b.

Step 1212 generates recommendations to the user based on the analysis of the classified oral pH data. The recommendations are communicated to the user 1202 using machine learning module 136. For instance, the recommendations generated and communicated to the user 1202 may be "eat less oily food, sleep on your left position". These are some general recommendations provided by the machine learning module 136, which may differ based on the severity of the acidic reflux conditions 1208b.

Figure 13:
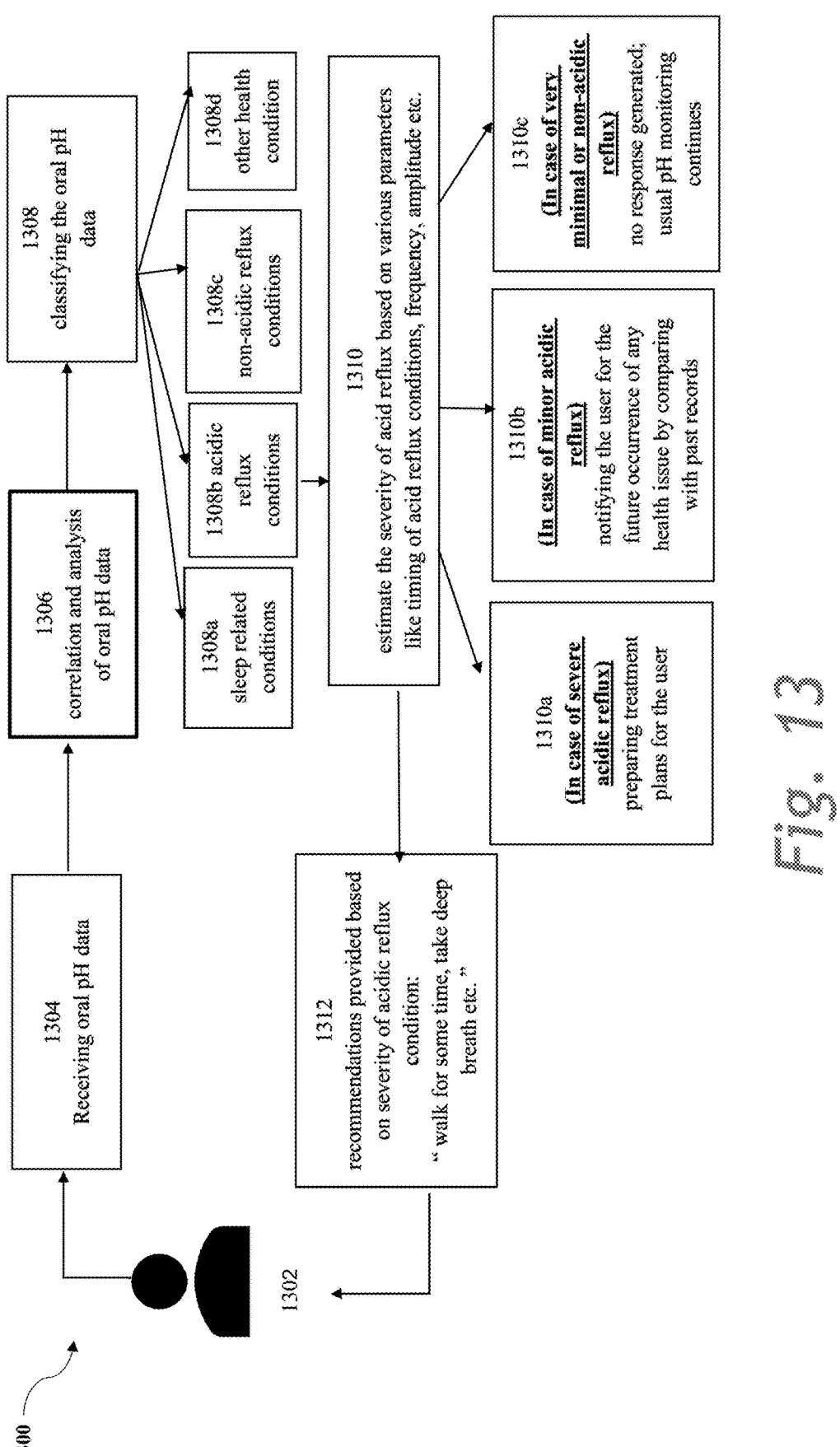
FIG. 13 illustrates another example method of monitoring pH using an intraoral device and analyzing the processed oral pH data, in accordance with one implementation of the present disclosure.

FIG. 13 illustrates another example method of monitoring pH using an intraoral device and analyzing the processed oral pH data, in accordance with one implementation of the present disclosure.

The exemplary method, for instance, is performed at least in part in the context of the environment 100. As shown in the figure, the intraoral device 102 is placed within the oral cavity of the user 1302. Further, at 1304, the oral pH data is received from the pH sensor placed within an intraoral device 102. The device module 120 of FIG. 1, for instance, receives oral pH data from the sensors 116. At step 1306, the oral pH data is correlated with one or more user related data to classify the oral pH data into one or more pre-defined categories indicative of a health condition. For instance, the user related data may include user id, date, time, user health related details, device details and so on. The device module 120, for instance, correlates the oral pH data along with the user related data.

At step 1308, the oral pH data is classified based on plurality of health conditions. These health conditions include sleep related conditions 1308a, acidity reflux conditions 1308b, non-acidic reflux conditions 1308c and other health conditions 1308d. The other health conditions 1308d may include oral health related conditions, tooth decay related conditions and so on. The machine learning module 136 performs the process of classification of the oral pH data.

At step 1310, the severity of acid reflux condition 1308b is estimated based on various parameters like timing of acid reflux conditions 1308b, frequency, amplitude etc. It further classifies the severity of the acid reflux conditions 1308b into one or more pre-defined categories such as severe acidic reflux, minor acidic reflux or minimal or non-acidic reflux. Based on the mentioned classification, the machine learning module 136 generates feedback and/or recommendations. For instance, the user 1302 is suffering from sleep apnea or other sleep related issues and is facing acidity reflux conditions 1308b during sleep. During the case of acidity condition 1308b during the sleep, the pH sensor placed inside the oral cavity of the user 1302 will detect the change in the pH level and start receiving the oral pH data as shown in Step 1304. The machine learning module 136 will generate feedback, which may be in the form of notification to the third-party application or a direct communication to the user 1302 or physician or any other healthcare professional. The feedback provided to the user 1302 depends on the severity of the acid reflux condition 1308b. For instance, if it is a severe acidic reflux condition then the feedback 1310a provided to the user 1302 may include "preparing a treatment plan for the user". This may include change in the medications or any other treatment plan as suggested by the doctor/physician, as the severity is high in this case. Similarly, if the severity is minor or medium, the feedback 1310b provided to the user 1302 may include "notifying the user for the future occurrence of health issues by comparing with the past record". The past health record of the user is compared with the currently generated oral pH data and the user is notified based on the matching results about the future occurrence of any health conditions. Based on such notifications, the user 1302 may start taking precautionary measures in order to avoid the occurrence of any health issues. Further, if the severity is minimal or non-acidic reflux condition 1308c is monitored, then no feedback will be generated and the intraoral device 102 will continue to monitor the pH of the user 1302.

Step 1312 generates recommendations to the user based on the analysis of the classified oral pH data and the severity of the conditions monitored. The recommendations are generated and communicated to the user 1302 using machine learning module 136. For instance, the recommendations generated and communicated to the user 1302 may be "walk for some time, take deep breath". Such a recommendation is made in case the severity is very less. These are some general recommendations provided by the machine learning module 136, which may differ based on the severity of the acidic reflux condition 1308b.

FIG. 14 depicts an example method 1400 for utilizing oral pH data obtained as part of intraoral monitoring in accordance with one or more implementations. The method, for instance, is performed at least in part in the context of the environment 100 and can be implemented in conjunction with the method 1100.

At step 1402, oral pH data generated by an intraoral device is received. The DVMP 108 is operatively coupled to an intraoral device 102, which allows transfer of oral pH data from intraoral device 102 to the DVMP 108. The DMP 110, for instance, receives oral pH data from the DVMP 108. The oral pH data is correlated with other user related data like date, time, user ID, user health details, device details and so on. Further, the oral pH data may be encoded and/or encrypted to protect the data.

At step 1404, a query for oral pH data is received. In implementation, the RMS 112, for instance queries the DMP 110 for a report based on a time a user wears the intraoral device 102. At step 1406, a report based on the oral pH data is generated. The DMP 110, for instance, generates a report that correlates various sensor data such as based on time and date at which the oral pH data was received.

At step 1408, a notification of the report is generated. The RMS 112, for instance, determines that the report is available and can generate and communicate a notification of the report, such as to a clinician and/or other personnel. Accordingly, during an appointment with the user (or anytime) a clinician may review the report and provide useful information to that user.

Hence, by using an analytical equation and/or machine learning technique to analyze the oral pH data, the oral pH data can be classified to accurately identify different stages of sleep. As such, a report generated by the RMS 112 can be used for various purposes, such as monitoring and diagnostic purposes.

FIG. 15 depicts an example method 1500 for intraoral monitoring in accordance with one or more implementations. The method, for instance, is performed at least in part in the context of the environment 100. At step 1502, detection of an intraoral device 102 placed within a docking station 104 is performed. A user, for instance, places the intraoral device 102 within the docking station 104 and latches the door 902. The docking station 104 can transmit a signal in response to the door 902 being closed, such as to the monitor app 132. The intraoral device 102 initiates taking any action at step 1504. For instance, in response to the intraoral device 102 being placed into the docking station 104 and the door 902 being latched closed, the device module 120 of the docking station 104 initiates actions such as battery charging, cleaning, sensor data transmission, and so forth. Further, the DVMP 108 is notified of the locking event and in response requests oral pH data from the device module 120.

At step 1506, provision oral pH data is received by the intraoral device 102. The docking station 104, for instance, provisions the data to the DVMP 108 in an ordered fashion such as to preserve battery power, allow post-processing of information in the appropriate location, and so forth. In at least one implementation the DMP 110 can provision the oral pH data to the RMS 112 and notify a clinician and/or other personnel of updated oral pH data, trends, and other extracted insights.

At step 1508, provisions data to the intraoral device 102. The DVMP 108, for instance, provisions data to the intraoral device 102 via the docking station 104, such as for authentication requests, firmware updates, and so forth. In at least one implementation the DVMP 108 may send updated data generated at step 1506 to the intraoral device 102 in order to execute a calibration activity that accounts for previous data errors and/or performs sensor calibration to be more accurate, etc.

Security-Based Attributes

Generally, information received by the intraoral device 102 is collected with consent from the unique user. When the intraoral device 102 is manufactured independently it is assigned an identifier, serial number. An intraoral device 102 that is paired with a unique user of the intraoral device 102. Each unique user gives consent for the present system to collect, transmit, analyze. Only users with authorized permission(s) to collect, view, evaluate, share, distribute, and analyze unique user Data are allowed. Data transmission from any portion of the present system to another is encrypted throughout the entirety of its life within the present system.

In at least one implementation, block-chain techniques can be utilized as part of user data storage, transfer, and access, which can improve data security, privacy, and data accessibility of various users of the described systems. For instance, attributes of block-chain including cryptography, decentralization, and consensus, ensure trust in transactions that involve health-related data. Utilizing the described techniques, for example, user data is structured into blocks and each block contains a health-related transaction or bundle of transactions. Further, each new block connects to all the blocks before it in a cryptographic chain in such a way that greatly decreases the ability to tamper with the data. Health data-related transactions within the blocks can be validated and agreed upon by a consensus mechanism, which can ensure that each transaction is valid.

FIG. 16 depicts an example method 1600 for security attributes as part of intraoral monitoring in accordance with one or more implementations. The method, for instance, is performed at least in part in the context of the environment 100 and can be implemented in conjunction with the methods 1100, 1400 and 1500.

An intraoral device 102 for a unique user is fabricated at 1602. An authorized manufacturer, for instance, manufactures an intraoral device 102 for a specific user. The user logs into a data management platform 110 using an authentication process at 1604. The manufacturer, for instance, logs into the DMP 110. At step 1606, a user file within the data management platform 110 is created. The user file, for instance, includes a first name, last name, date of birth, and/or other unique user information. At step 1608, the serial number associated with an intraoral device 102 is entered into a specific user file within the data management platform 110. At step 1610, the pairing of the intraoral device 102 is done. The manufacturer, for instance, confirms the pairing of the intraoral device 102 and the user device.

The example methods described above are performable in various ways, such as for implementing different aspects of the systems and scenarios described herein. Generally, any services, components, modules, methods, and/or operations described herein are able to be implemented using software, firmware, hardware (e.g., fixed logic circuitry), manual processing, or any combination thereof. Some operations of the described methods, for example, are described in the general context of executable instructions stored on computer-readable storage memory that is local and/or remote to a computer processing system, and implementations include software applications, programs, functions, and the like. Alternatively, or in addition, any of the functionality described herein is performable, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like. The order in which the methods are described is not intended to be construed as a limitation, and any number or combination of the described method operations are able to be performed in any order to perform a method, or an alternate method.

Consider now an example system and device that are able to be utilized to implement the various techniques described herein.

Example System and Device

FIG. 17 illustrates an example system 1700 that includes an example computing device 1702 representative of one or more computing systems and/or devices that are usable to implement the various techniques described herein. The computing device 1702 includes, for example, a server of a service provider, a device associated with a client (e.g., a client device), an on-chip system, and/or any other suitable computing device or computing system.

The example computing device 1702 as illustrated includes a processing system 1704, one or more computer-readable media 1706, and one or more Input/output (I/O) interface(s) 1708 that are communicatively coupled, one to another. Although not shown, the computing device 1702 further includes a system bus or other data and command transfer system that couples the various components, one to another. For example, a system bus includes any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 1704 is representative of functionality to perform one or more operations using hardware. Accordingly, the processing system 1704 is illustrated as including hardware elements 1710 that can be configured as processors, functional blocks, and so forth. This includes example implementations in hardware as an application specific integrated circuit or other logic device formed using one or more semiconductors. The hardware elements 1710 are not limited by the materials from which they are formed or the processing mechanisms employed therein. For example, processors are comprised of semiconductor(s) and/or transistors (e.g., electronic integrated circuits (ICs)). In such a context, processor-executable instructions are, for example, electronically-executable instructions.

The computer-readable media 1706 is illustrated as including memory/storage 1712. The memory/storage 1712 represents memory/storage capacity associated with one or more computer-readable media. In one example, the memory/storage 1712 includes volatile media (such as random-access memory (RAM)) and/or nonvolatile media (such as read only memory (ROM), Flash memory, optical disks, magnetic disks, and so forth). In another example, the memory/storage 1712 includes fixed media (e.g., RAM, ROM, a fixed hard drive, and so on) as well as removable media (e.g., Flash memory, a removable hard drive, an optical disc, and so forth). The computer-readable media 1706 is configurable in a variety of other ways as further described below.

Input/output interface(s) 1708 are representative of functionality to allow a user to enter commands and information to computing device 1702, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which employs visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 1702 is configurable in a variety of ways as further described below to support user interaction.

Various techniques are described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques are implementable on a variety of commercial computing platforms having a variety of processors.

Implementations of the described modules and techniques are storable on or transmitted across some form of computer-readable media. For example, the computer-readable media includes a variety of media that is accessible to the computing device 1702. By way of example, and not limitation, computer-readable media includes "computer-readable storage media" and "computer-readable signal media."

"Computer-readable storage media" refers to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable, and non-removable media and/or storage devices implemented in a method or technology suitable for storage of information such as computer readable instructions, data structures, program modules, logic elements/circuits, or other data. Examples of computer-readable storage media include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which are accessible to a computer.

"Computer-readable signal media" refers to a signal-bearing medium that is configured to transmit instructions to the hardware of the computing device 1702, such as via a network. Signal media typically embodies computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 1710 and computer-readable media 1706 are representative of modules, programmable device logic and/or fixed device logic implemented in a hardware form that is employable in some embodiments to implement at least some aspects of the techniques described herein, such as to perform one or more instructions. Hardware includes components of an integrated circuit or on-chip system, an application-specific integrated circuit (ASIC), a field-programmable gate array (FPGA), a complex programmable logic device (CPLD), and other implementations in silicon or other hardware. In this context, hardware operates as a processing device that performs program tasks defined by instructions and/or logic embodied by the hardware as well as a hardware utilized to store instructions for execution, e.g., the computer-readable storage media described previously.

Combinations of the foregoing are also employable to implement various techniques described herein. Accordingly, software, hardware, or executable modules are implementable as one or more instructions and/or logic embodied on some form of computer-readable storage media and/or by one or more hardware elements 1710. For example, the computing device 1702 is configured to implement particular instructions and/or functions corresponding to the software and/or hardware modules. Accordingly, implementation of a module that is executable by the computing device 1702 as software is achieved at least partially in hardware, e.g., through use of computer-readable storage media and/or hardware elements 1710 of the processing system 1704. The instructions and/or functions are executable/operable by one or more articles of manufacture (for example, one or more computing devices 1702 and/or processing systems 1704) to implement techniques, modules, and examples described herein.

The techniques described herein are supportable by various configurations of the computing device 1702 and are not limited to the specific examples of the techniques described herein. This functionality is also implementable entirely or partially through use of a distributed system, such as over a "cloud" 1714 as described below.

The cloud 1714 includes and/or is representative of a platform 1716 for resources 1718. The platform 1716 abstracts underlying functionality of hardware (e.g., servers) and software resources of the cloud 1714. For example, the resources 1718 include applications and/or data that are utilized while computer processing is executed on servers that are remote from the computing device 1702. In some examples, the resources 1718 also include services provided over the Internet and/or through a subscriber network, such as a cellular or Wi-Fi network.

The platform 1716 abstracts the resources 1718 and functions to connect the computing device 1702 with other computing devices. In some examples, the platform 1716 also serves to abstract scaling of resources to provide a corresponding level of scale to encountered demand for the resources that are implemented via the platform. Accordingly, in an interconnected device embodiment, implementation of functionality described herein is distributable throughout the system 1700. For example, the functionality is implementable in part on the computing device 1702 as well as via the platform 1416 that abstracts the functionality of the cloud 1714.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

Technical Advancements:

The present disclosure described herein above for tracking and management of condition in patients has several technical advantages including, but not limited to, the realization of:

provides customized feedback and/or recommendations based on matching the profile of the user with other user of similar health conditions or based on the analyzed oral pH data;

suitable for predicting the stage of progression of condition and the future events;

monitor one's health at their convenience;

portable and light weight;

improves patient safety through direct access to the medical history, treatments online;

provides timely, better and cheaper access to information;

works without continuous electricity;

user friendly;

easy to use;

maintains transparency and security of the data;

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

We claim:

1. An intraoral device for monitoring pH comprising:
a flexible substrate;
a plurality of sensors including at least one pH sensor configured to generate an oral pH data;
a device module configured to:
receive the oral pH data from the at least one pH sensor;
correlate the oral pH data with one or more user related data to classify the oral pH data into one or more pre-defined categories indicative of at least one health condition, wherein the user related data includes a pre-stored user data and/or a real-time generated user data;
generate at least one or more feedback and/or recommendation for the user, based on a classification of the oral pH data into the one or more pre-defined categories, wherein the generated feedback and/or recommendation is appropriate to manage the at least one health condition;
communicate the oral pH data and/or the at least one or more feedback and/or recommendation to an external device communicatively coupled to the intraoral device;
wherein the at least one pH sensor further comprises at least a sensing electrode and a reference electrode such that a shape of the sensing electrode is different from the reference electrode, wherein the difference in shape enhances a contact area between the sensing electrode and salivary glands which increases a sensitivity of the at least one pH sensor.

2. The intraoral device as claimed in claim 1, wherein the said flexible substrate is formed from a flexible material such as Kapton™ tape and/or other flexible material, such as a flexible polymer.

3. The intraoral device as claimed in claim 1 is formed using cyclic voltammetry, wherein a methodology used is a low temperature fabrication process.

4. The intraoral device as claimed in claim 1, wherein the pH sensor comprises a sensor array that includes at least one sensing electrode and at least one reference electrode placed adjacent to each other such that the sensing electrode and the reference electrode are embedded on the flexible substrate and are placed equidistant from each other.

5. The sensor array as claimed in claim 4, wherein the sensing electrode is formed from biocompatible material like Iridium (Ir) or Iridium Oxide (IrOx) or Antimony (Sb) and the reference electrode is made from Platinum (Pt).

6. The intraoral device as claimed in claim 1, wherein the intraoral device can be placed either on upper jaw or on lower jaw at a posterior of teeth and the sensing electrode and reference electrodes are facing a tongue.

7. The intraoral device as claimed in claim 1, wherein the one or more health conditions include sleep related conditions, GERD condition, acid reflux conditions, oral health conditions and so on.

8. The intraoral device as claimed in claim 1, wherein the said device module is configured to collect the oral pH data and communicates the oral pH data to various entities to perform health monitoring related to one or more health conditions like sleep stage monitoring, sleep apnea detection, GERD monitoring, acid reflux tracking etc. and provide at least appropriate feedback and/or recommendations to the user related to a disease and/or health condition.

9. The intraoral device as claimed in claim 1, wherein the said device module can be implemented as one or more microprocessors, microcomputers, microcontrollers, digital signal processors, central processing units, state machines, logic circuitries, and/or any devices that manipulate signals based on operational instructions.

10. A method of monitoring pH using an intraoral device comprising:
receiving, an oral pH data from at least one pH sensor embedded within the intraoral device by calculating a electric potential difference between a reference electrode and a sensing electrode placed within a sensor array;
correlating, the oral pH data with one or more user related data to classify the oral pH data into one or more pre-defined categories indicative of a health condition;
generating, at least one or more feedback and/or recommendation for the user using a machine learning model, based on a classification of the oral pH data into the one or more pre-defined categories, wherein the generated feedback and/or recommendation is appropriate to manage the at least one health condition;
communicating, the oral pH data and/or at least one recommendation and/or feedback from the intraoral device to an external device and/or person via a wireless and/or wired data transmission;
wherein the at least one pH sensor further comprises at least a sensing electrode and a reference electrode such that a shape of the sensing electrode is different from the reference electrode, wherein the difference in shape enhances a contact area between the sensing electrode and salivary glands which increases a sensitivity of the at least one pH sensor.

11. The method of monitoring pH using an intraoral device as claimed in claim 10, wherein a device module is configured to process the real time sensed data by employing machine learning techniques like Gradient boosted techniques, Decision tree techniques and Logistic regression techniques to receive and store the data corresponding to the oral pH data associated with said users and is further configured to classify the oral pH data corresponding to the one or more health conditions associated with the said user using Information Communication Technology (ICT) techniques.

12. The method of monitoring pH using an intraoral device as claimed in claim 10, wherein the user related data includes date, time, user id, user health related details, device details etc.

13. The method of monitoring pH using an intraoral device as claimed in claim 10, wherein the communicated oral pH data may be encoded and/or encrypted for data security.

14. The method of monitoring pH using an intraoral device as claimed in claim 10, uses block-chain techniques as part of user data storage, communication, and access, which can improve data security, privacy, and data accessibility of various users.

15. A system for monitoring intraoral pH comprising:

an intraoral device consisting of: (1) a flexible substrate; and (2) a plurality of sensors including at least one pH sensor configured to receive an oral pH data;

a DVMP (device management platform), operatively coupled to the intraoral device to receive the oral pH data from the intraoral device;

a DMP (data management platform), configured to receive the oral pH data from the DVMP (device management platform) to correlate the oral pH data with one or more user related data;

a docking station, configured to perform one or more functionalities for maintaining and interfacing with the intraoral device;

a machine learning module, configured to analyse and classify the oral pH data into one or more pre-defined categories indicative of at least one health condition, wherein the machine learning module generates at least one feedback and/or recommendations related to the one or more health condition based on an analysis and classification of the oral pH data;

a client device, configured to receive the oral pH data and/or at least one recommendation and/or feedback related to the one or more health conditions of the user;

wherein the at least one pH sensor further comprises at least a sensing electrode and a reference electrode such that a shape of the sensing electrode is different from the reference electrode, wherein the difference in shape enhances a contact area between the sensing electrode and salivary glands which increases a sensitivity of the at least one pH sensor.

16. The system for monitoring pH as claimed in claim 15, wherein the DMP, DVMP, the docking station and the client device are operatively connected to the intraoral device via network or direct device to device connectivity.

17. The system for monitoring pH as claimed in claim 15, wherein the client device includes a monitor application (App) which is configured to update and reconfigure the received correlated oral pH data and is further configured to enable data transfer to the intraoral device.

\* \* \* \* \*